United States Patent
Maycotte et al.

(10) Patent No.: US 10,652,248 B2
(45) Date of Patent: May 12, 2020

(54) SYSTEMS AND METHODS OF MANAGING DATA RIGHTS AND SELECTIVE DATA SHARING

(71) Applicant: Molecula Corp., Austin, TX (US)

(72) Inventors: Higinio O. Maycotte, Austin, TX (US); Travis Turner, Austin, TX (US); Troy Lanier, Austin, TX (US)

(73) Assignee: Molecula Corp., Austin, TX (US)

( * ) Notice: Subject to any disclaimer, the term of this patent is extended or adjusted under 35 U.S.C. 154(b) by 0 days.

(21) Appl. No.: 15/222,683

(22) Filed: Jul. 28, 2016

(65) Prior Publication Data

US 2018/0034824 A1 Feb. 1, 2018

(51) Int. Cl.
| | |
|---|---|
| *H04L 29/06* | (2006.01) |
| *G06F 16/27* | (2019.01) |
| *G06F 16/22* | (2019.01) |
| *G06F 21/62* | (2013.01) |
| *G06Q 50/22* | (2018.01) |
| *H04L 29/08* | (2006.01) |

(52) U.S. Cl.
CPC ........ *H04L 63/102* (2013.01); *G06F 16/2237* (2019.01); *G06F 16/2282* (2019.01); *G06F 16/27* (2019.01); *G06F 21/6218* (2013.01); *G06F 21/6263* (2013.01); *G06Q 50/22* (2013.01); *H04L 63/06* (2013.01); *H04L 67/1095* (2013.01)

(58) Field of Classification Search
CPC .................................................... H04L 63/102
USPC ......................................................... 726/26
See application file for complete search history.

(56) References Cited

U.S. PATENT DOCUMENTS

| | | | |
|---|---|---|---|
| 5,751,949 A | 5/1998 | Thomson et al. | |
| 5,870,765 A | 2/1999 | Bauer et al. | |
| 5,884,307 A * | 3/1999 | Depledge | G06F 17/30312 |
| 5,940,818 A | 8/1999 | Malloy et al. | |
| 6,236,996 B1 | 5/2001 | Bapat et al. | |
| 6,275,824 B1 | 8/2001 | O'Flaherty et al. | |
| 2002/0087633 A1 | 7/2002 | Nelson | |
| 2003/0191743 A1 | 10/2003 | Brodersen et al. | |
| 2004/0193879 A1 * | 9/2004 | Sonoda | G06Q 10/30 |
| | | | 713/165 |
| 2005/0044426 A1 | 2/2005 | Vogel et al. | |
| 2005/0050054 A1 | 3/2005 | Clark et al. | |
| 2006/0034277 A1 * | 2/2006 | Jang | H04L 1/1614 |
| | | | 370/389 |

(Continued)

*Primary Examiner* — Peter C Shaw

(74) *Attorney, Agent, or Firm* — Kowert, Hood, Munyon, Rankin & Goetzel, P.C.

(57) ABSTRACT

A method includes receiving an access request at a first computing device from a second computing device, the access request specifying a data structure, the data structure including first data stored in a first portion of the data structure and second data stored in a second portion of the data structure. The method also includes extracting a first key from the access request and identifying a data rights definition that is associated with the data structure and that is associated with a second key, the data rights definition indicating that the first data but not the second data is shared with an entity associated with the second computing device. The method further includes comparing the first key to the second key, and, based on the comparison, determining whether to grant the second computing device access to the first data but not the second data.

19 Claims, 19 Drawing Sheets

(56) References Cited

U.S. PATENT DOCUMENTS

| | | | |
|---|---|---|---|
| 2006/0123010 A1* | 6/2006 | Landry | G06F 16/25 |
| 2008/0082540 A1 | 4/2008 | Weissman et al. | |
| 2008/0229117 A1* | 9/2008 | Shin | G06F 21/123 |
| | | | 713/190 |
| 2009/0248616 A1 | 10/2009 | Molini | |
| 2010/0146609 A1* | 6/2010 | Bartlett | G06Q 20/02 |
| | | | 726/7 |
| 2011/0060916 A1* | 3/2011 | Faitelson | G06F 21/6218 |
| | | | 713/189 |
| 2011/0093925 A1* | 4/2011 | Krishnamoorthy | |
| | | | G06F 21/6218 |
| | | | 726/4 |
| 2011/0276584 A1* | 11/2011 | Cotner | G06F 17/30008 |
| | | | 707/769 |
| 2011/0296113 A1* | 12/2011 | Elnozahy | G06F 11/1456 |
| | | | 711/130 |
| 2012/0197840 A1* | 8/2012 | Oliver | G06F 16/27 |
| | | | 707/613 |
| 2016/0380677 A1* | 12/2016 | Moro | A63F 13/69 |
| | | | 455/41.1 |
| 2017/0300507 A1* | 10/2017 | Kataoka | G06F 16/316 |
| 2017/0339150 A1* | 11/2017 | Barsness | H04L 63/1425 |

\* cited by examiner

126 ⤵

|    | C1 | C2 | C3 | C4 | C5 | C6 | C7 |
|----|----|----|----|----|----|----|----|
| R1 | ▓  | ▓  |    |    |    |    |    |
| R2 | ▓  | ▓  |    |    | B1 |    |    |
| R3 | ▓  | ▓  |    |    |    |    |    |
| R4 | ▓  | ▓  |    |    |    |    | B2 |
| R5 | ▓  | ▓  | ▓  | ▓  | ▓  | ▓  | ▓  |
| R6 | ▓  | ▓  | ▓  | ▓  | ▓  | ▓  | ▓  |
| R7 | ▓  | ▓  |    |    |    |    |    |

200 ⤵

Data Rights Definition

Grantor: First Entity
Grantee: Second Entity
Data Structure: Bitmap Index 126
Data to be shared: R5-R6, C1-C2, B1-B2
Rights: Read-Only (R5-R6, C1-C2, B1-B2)
Personally Identifiable Information: Yes (C1-C2, B1-B2), No (R5-R6)
Validity Time Period: Until 12/31/2020
Key: r6t!{*!J0<yC5lQoXm155=2#oeKF'4S}0f;6ls8'Y,Eg{3O<0m8vc9=3Mt2n7~p

SYSTEMS AND METHODS OF MANAGING DATA RIGHTS AND SELECTIVE DATA SHARING

BACKGROUND

Computer networks, such as public networks (e.g., the Internet) and private networks (e.g., at medical institutions, financial institutions, business enterprises, etc.) have become a medium for research, communication, distribution, and storage of data. Consequently, more and more devices are network-enabled. To illustrate, on any given day, a typical user may access a half-dozen or more network-enabled devices, such as their mobile phone, tablet computer, home security system devices, one or more wearable devices, a home laptop or desktop, a work laptop or desktop, and home entertainment devices (e.g., televisions, game consoles, set top boxes, etc.). Moreover, Internet of Things (IoT) protocols enable network-enabled devices to communicate with each other without user intervention. Thus, there is an increasing amount of data being accessed, transferred, and stored online. As users use networks to access data, they also generate a large amount of data regarding themselves. On websites such as social networks, users actively and willingly share data regarding themselves. Thus, at any given time, different subsets of data regarding a user or a group of users may be available online. However, it may be difficult to share data across data aggregators or websites to gain a more "complete" understanding of a user due to privacy concerns and/or technological incompatibilities (e.g., incompatible data storage formats across different aggregators or websites). In addition, data sharing may be limited to an "all-or-nothing" model, i.e., a website or aggregator may have only two choices regarding data sharing: share all data regarding all users, or share no data regarding any user.

SUMMARY

Systems and methods of managing data rights and enabling selective data sharing are disclosed. The techniques of the present disclosure may enable selectively sharing some, but not all, of the data stored in a data structure, such as a table, a database and/or a bitmap index. The disclosed selective sharing of arbitrarily selected part(s) of a data structure may provide a more granular data sharing approach than "all-or-nothing" systems, and may be more efficient than systems in which data to be shared is duplicated to a new data structure so that (the entirety of) the new data structure can be shared.

The bitmap index may enable real-time or near-real-time computation of various metrics or queries that combine logical set operations, such as AND, OR, and NOT operations. When the underlying data set is large, the bit strings of the bitmap index may be stored in distributed fashion across multiple network-attached storage nodes, and executing queries on the bitmap index may involve parallel computations on multiple storage nodes. In particular examples, the bitmap index includes metadata name-value pairs. Inclusion of such metadata within the bitmap index may enable generating query results without having to perform lookup operations on external data structures.

In accordance with at least one described embodiment, a method includes receiving an access request at a first computing device from a second computing device, the access request specifying a data structure, the data structure including first data stored in a first portion of the data structure and second data stored in a second portion of the data structure. The method also includes extracting a first key from the access request and identifying a data rights definition that is associated with the data structure and that is associated with a second key, the data rights definition indicating that the first data but not the second data is shared with an entity associated with the second computing device. The method further includes comparing the first key to the second key, and, based on the comparison, determining whether to grant the second computing device access to the first data but not the second data.

Aspects of the present disclosure may include one or more of the following:

The data structure may be stored at the first computing device.

The data structure may be stored remote to the first computing device.

The data structure may include a database table.

The data structure may include a bitmap index.

The bitmap index may include a plurality of bit strings, where a value stored in a particular location in each of the bit strings indicates whether a corresponding signal associated with a signal source has been received.

The signal source may correspond to a user, to an electronic device associated with the user, or an internet of things (IoT) device.

The bitmap index may store data associated with at least one demographic attribute, at least one behavior, at least one brand affinity, or a combination thereof.

The bitmap index may store data associated with at least one patient, medical staff, medical equipment, at least one medical location, at least one medicine, at least one healthcare event, at least one medical attribute, or any combination thereof.

The bitmap index may store data associated with at least one investor, at least one financial advisor, at least one financial product, at least one account, at least one investment, or any combination thereof.

The bitmap index may store data associated with at least one interne of things (IoT) device, at least one sensor reading, at least one communication by the IoT device, at least one status of the IoT device, at least one event observed by the IoT device, or any combination thereof.

The bitmap index stores data associated with at least one customer, at least one product in inventory, or any combination thereof.

The data rights definition may be stored in a repository that stores a plurality of data rights definitions associated with a plurality of data structures and a plurality of entities.

At least a portion of the data rights definition may be stored in the data structure.

The data rights definition may further indicate whether the entity associated with the second computing device has read-only access to the first data or read-write access to the first data, that the first data is shared with the entity associated with the second computing device for a particular time period, whether personally identifiable information associated with the first data is shared with the entity associated with the second computing device, or any combination thereof.

Granting access to the first data may include sending a copy of the first data to the second computing device for storage in a second data structure at the second computing device.

The method may further include receiving a write operation with respect to the first data, and causing the write operation to be replicated at the copy of the first data in the second data structure.

The write operation may be replicated responsive to a push synchronization operation initiated by the first computing device or responsive to a pull synchronization operation initiated by the second computing device or by another computing device associated with the entity.

In another particular embodiment, an apparatus includes a processor and a memory storing instructions executable by the processor to perform operations including receiving an access request at a first computing device from a second computing device, the access request specifying a data structure, the data structure including first data stored in a first portion of the data structure and second data stored in a second portion of the data structure. The operations also include extracting a first key from the access request and identifying a data rights definition that is associated with the data structure and that is associated with a second key, the data rights definition indicating that the first data but not the second data is shared with an entity associated with the second computing device. The operations further include comparing the first key to the second key and, based on the comparison, determining whether to grant the second computing device access to the first data but not the second data.

In another particular embodiment, a computer-readable storage device stores instructions that, when executed, cause a computer to perform operations including receiving an access request at a first computing device from a second computing device, the access request specifying a data structure, the data structure including first data stored in a first portion of the data structure and second data stored in a second portion of the data structure. The operations also include extracting a first key from the access request and identifying a data rights definition that is associated with the data structure and that is associated with a second key, the data rights definition indicating that the first data but not the second data is shared with an entity associated with the second computing device. The operations further include comparing the first key to the second key and, based on the comparison, determining whether to grant the second computing device access to the first data but not the second data.

BRIEF DESCRIPTION OF THE DRAWINGS

FIG. 2 is a diagram to illustrate a particular embodiment of a data rights definition;

DETAILED DESCRIPTION

Figure 1:
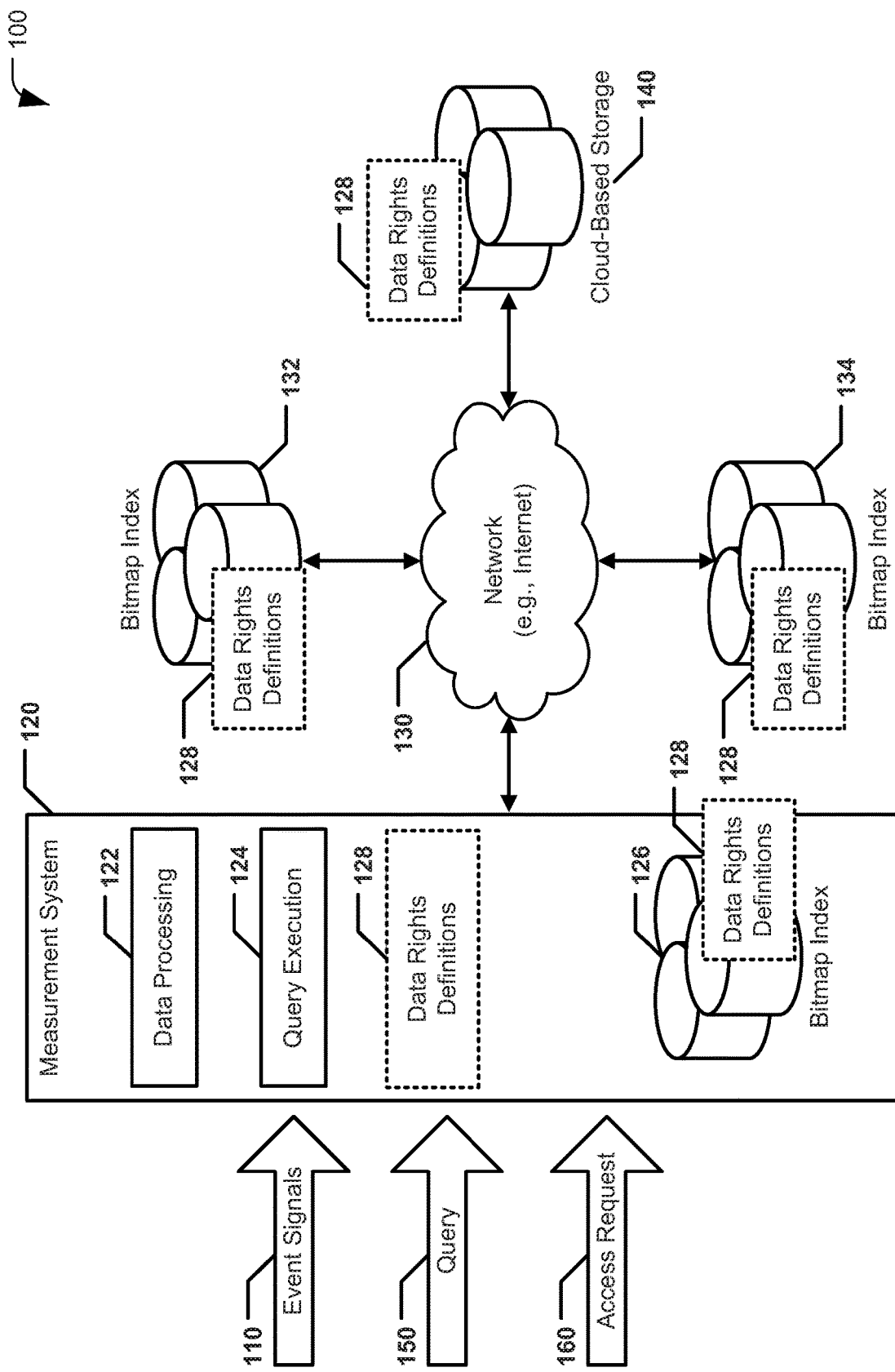
FIG. 1 is a diagram to illustrate a particular embodiment of a system that is operable to manage data rights and enable selective data sharing.

FIG. 1 illustrates a particular embodiment of a system 100 including a measurement system 120 configured to receive event signals 110 associated with the audience of one or more media properties (e.g., websites). The event signals 110 may be received from sources that include, but are not limited to, computing devices, mobile devices, web servers, measurement logs, third-party data sources, and social networks. It is to be understood that although various embodiments may be described herein in the context of audience measurement for media properties (e.g., websites), the present disclosure is not limited as such. A bitmap index may be used to represent data collected in other scenarios, including but not limited to sensor data, data from various Internet of Things (IoT) devices, genomic data, financial data, etc. In some examples, a bitmap index may represent data that is unrelated to Internet use. For example, a bitmap index may be used to represent static data sets that are uploaded to the measurement system 120 offline, and may correspond to data that was not captured/generated digitally, even though such data is represented digitally in the bitmap index. The systems and methods of the present disclosure may thus be agnostic as to the origin and type of data being represented by a bitmap index.

The measurement system 120 may be implemented using one or more computing devices (e.g., servers). For example, such computing devices may include one or more processors or processing logic, memories, and network interfaces. The memories may include instructions executable by the processors to perform various functions described herein. The network interfaces may include wired and/or wireless interfaces operable to enable communication to local area networks (LANs) and/or wide area networks (WANs), such as the Internet. In the illustrated example, the measurement system 120 is communicably coupled to a network 130.

The event signals 110 may include information associated with audience members of a media property. For example, when an audience member creates an account or otherwise registers with a media property using social networking identification, the measurement system 120 may retrieve event signals corresponding to data stored in social networking profiles of the audience member. As another example, the event signals 110 may identify specific interactions by the audience members with respect to the media property (e.g., what action was taken at a media property, when the action was taken, for how long the action was taken, etc.). The interactions may include interactions with advertisements presented by the media property and/or interactions with content presented by the media property. In a particular embodiment, each of the event signals 110 identifies a property (e.g., "Property 1") and an audience member (alternately referred to herein as a "user"). For example, if a user having a user ID=N made a purchase on the website for Property 1, a corresponding event signal received by the measurement system 120 may be "(userID=N, property='Property 1', behavior=Purchase)". In some examples, an event signal may also include metadata regarding an audience member and/or an attribute. In alternate embodiments, a different format may be used to represent an event signal. In some embodiments, an event signal includes an alphanumeric key (e.g., a cryptographically generated value) that is verified by the measurement system 120, as further described herein, before taking any other actions regarding the event signal.

The measurement system 120 may include a data processing module 122 and a query execution module 124, each of which may be implemented using instructions executable by one or more processors at the measurement system 120. The data processing module 122 may receive the event signals 110 and store "raw" data corresponding to the event signals 110 (e.g., a copy of the event signals 110) in cloud-based storage 140. The data processing module 122 may also store indexing data for the cloud-based storage 140 in a bitmap index 126. In a particular embodiment, unlike the cloud-based storage 140, the bitmap index 126 may be local (or more quickly accessible) to the measurement system 120. To illustrate, data for the bitmap index 126 may be stored across one or more data storage devices (e.g., nodes) that are part of the measurement system 120 or accessible to the measurement system 120 via a LAN, or other private high-speed network, as opposed to a WAN. Alternatively, or in addition, data of the bitmap index 126 may be stored "in-memory," such as in RAM. Thus, read and write operations with respect to the bitmap index 126 may be faster than corresponding read and write operations with respect to the cloud-based storage 140.

The measurement system 120 may maintain a bitmap index 126 for each media property being measured. Data in the bitmap index 126 may be stored in the form of bit strings. The bitmap index 126 may store bit strings corresponding to at least a subset of the data stored in the cloud-based storage 140. Thus, depending on implementation, the bitmap index 126 may, for a particular media property, include bit strings for all of the data stored in the cloud-based storage 140 or less than all of the data stored in the cloud based storage 140. In a particular embodiment, the bitmap index 126 for a particular media property includes, for each audience member of the media property, data regarding one or more attributes of the audience member, which may include but are not limited to demographic attributes, brand affinities, behaviors (e.g., interactions with the media property), etc. It is to be understood that the techniques of the present disclosure may be used with bitmap indexes having an arbitrary number of rows (e.g., R, where R is an integer greater than or equal to one) and an arbitrary number of columns (e.g., C, where C is an integer greater than or equal to one).

To illustrate, a media property may have a known audience of one hundred thousand registered members. The bitmap index 126 for the media property may include bit strings representing various attributes associated with each of the hundred thousand audience members. Thus, each of the bit strings may be one hundred thousand bits in length. Further, the same location in each bit string may correspond to the same audience member. For example, if the $N^{th}$ location in a "Male" bit string has a value of "1" and the $N^{th}$ location in a "Watches video" bit string has a value of "1," this indicates that the $N^{th}$ audience member (who has a userID=N) is a male that has watched at least one video on the property.

In some examples, the bitmap index 126 for a media property may store bit strings corresponding to less than all of the data stored in the cloud-based storage 140. For example, although the cloud-based storage 140 may include "raw" data corresponding millions of signals (also referred to herein as "tiles"), the bitmap index 126 may store bit strings for a smaller subset of the most popular signals/tiles (e.g., the top fifty thousand signals/tiles). In an alternative embodiment, the bitmap index 126 may store bit strings for all of the signals/tiles tracked in the cloud-based storage 140. Examples of the bitmap index 126 are further described herein. In a particular embodiment, the bitmap index 126 is automatically sorted based on a parameter, such as the total count of asserted bits in each bit string, as an illustrative, non-limiting example.

The query execution module 124 may be configured to use the bitmap index 126 to execute queries regarding measurement data for a media property. For example, the query execution module 124 may receive a query 150 corresponding to the question "What are the top 50 tiles/signals for my audience?" In a particular embodiment, the query 150 may be generated using a query generation interface. If the bitmap index 126 is already sorted by the total number of asserted bits, the query execution module 124 may return data regarding the first fifty strings in the bitmap index 126.

Alternatively, if the bitmap index 126 is not sorted, the query execution module 124 may perform count operations on bit strings stored in the bitmap index 126. In a particular embodiment, because the bit strings may be stored across multiple nodes, the query execution module 124 may formulate a query execution plan that parallelizes execution of the query 150 across multiple nodes and minimizes the amount of data that is transferred between nodes during execution of the query 150. By executing the query 150 on bit strings stored in the bitmap index 126 in parallel without retrieving data from the cloud-based storage 140 and by reducing or minimizing data transfers, the query execution module 124 may achieve real-time or near-real-time performance. For example, the query execution module 124 may have a maximum query execution latency less than or equal to one hundred milliseconds. Further examples regarding query execution are described herein.

In particular aspects, the bitmap index 126 may store data associated with one or more media properties associated with a first entity (e.g., a user, group of users, or business organization), and the measurement system 120 may additionally include or have access to bitmap indexes 132, 134 that store data associated with one or more properties associated with a second entity and a third entity, respectively. In an alternative example, one or more of the bitmap indexes 132, 134 is included in or accessible to one or more other measurement systems instead of or in addition to the measurement system 120. The system 100 may enable an entity to share data stored in an arbitrarily specified portion of a data structure with another entity. For example, the first entity associated with the bitmap index 126 and the cloud-based storage 140 may share less than an entirety of the bitmap index 126 and/or data tables of the cloud-based storage 140 with the second entity (associated with the bitmap index 132) or the third entity (associated with the bitmap index 134).

To enable such data sharing, the system 100 may include data rights definitions 128, which may correspond to "data subscriptions" between the entities. FIG. 2 illustrates an example of an illustrative data rights definition 200 for the bitmap index 126. In the example of FIG. 2, the bitmap index 126 includes 7 rows (denoted R1-R7) and 7 columns (denoted C1-C7), although it is to be understood that in alternative examples, a bitmap index may include a different number of rows and/or a different number of columns. Two of the bits in the bitmap index are denoted B1 and B2, for illustrative purposes.

Data rights definitions may enable the first entity to share any combination of rows, columns, and bits with another entity. For example, the data rights definition 200 indicates that the first entity has shared the rows R5-R6, the columns C1-C2, and the bits B1-B2 with the second entity (in other examples, a portion of a row or column rather than an entire row or column may be shared). The data rights definition 200 indicates that the first entity is a grantor of the data rights and that the second entity is a grantee of the data rights. In alternative examples, more than one grantor and/or grantee may be indicated in a data rights definition. The data rights definition 200 also indicates that the second entity is being granted read-only access, until Dec. 31, 2020, to R5-R6, C1-C2, and B1-B2 of the bitmap index 126. The data rights definition 200 further indicates that personally identifiable information (PII) is being shared for C1-C2 and B1-B2, but not for R5-R6. Thus in an example, where each column represents a different user profile and each row represents a different tile/segment, PII (e.g., name, e-mail address, social networking profiles, etc.) may be shared for the users corresponding to C1-C2 and B1-B2.

The data rights definition 200 further includes a key. In the illustrated example, the key is a 504-bit key, although the key may be a different length in alternative embodiments. The key may be used by the second entity to gain access to the shared data. For example, the second entity (or a computing device associated therewith) may include the key in an access request for the shared data. The key included in the request may be extracted and compared to the key in the data rights definition 200, and access to the shared data may be granted based on the comparison (e.g., if the keys "match"). As used herein, keys may "match" if the keys are identical or if the keys can be verified by performing mathematical operations (e.g., as a in a public/private key pair). Thus, as used herein, a "data rights definition" may refer to data that indicates whether (and enables a computing device to determine whether) and in what fashion data is being shared by one entity with another entity, where such data may correspond to a portion of a data structure and need not correspond to an entirety of the data structure. In some examples, if a data rights definition indicates that first data stored in a first portion of a data structure is shared with an entity and is silent regarding second data stored in a second part of the data structure, this means that the second data is not being shared with the entity.

In some examples, a single data rights definition enables two-way data sharing (e.g., entity E1 shares a portion of data structure D1 with Entity E2, and Entity E2 shares a portion of data structure D2 with Entity E1). Alternatively, two-way sharing may be implemented via a pair of one-way data rights definitions.

Returning to FIG. 1, the data rights definitions 128, which in some examples may correspond to multiple data structures owned by multiple entities, may be stored in a repository that can be located in various places. For example, the data rights definitions may be stored in the measurement system 120, as part of one or more of the bitmap indexes 126, 132, 134, or in the cloud-based storage 140, as shown. Storing data rights definitions in a bitmap index may advantageously integrate both the data being shared and the access rights for the data into the same data structure, which may provide improved flexibility, faster data access time, and a smaller memory footprint than if the data rights definitions were stored separately from the data being shared. Conversely, storing data rights definitions at the measurement system 120 or in the cloud-based storage 140 may provide a convenient centralized repository for data rights information may provide reliability in situations where a data structure being shared (e.g., a bitmap index) becomes corrupted, because the data rights information is separate from the data structure.

During operation, the measurement system 120 may receive the event signals 110 from various event sources. Each event signal may include a unique identifier, such as a user ID. If the user is a "new" audience member, the user may be assigned a new user ID and a user profile may be created for the user. Data for the user profile may be stored in the cloud-based storage 140 and/or the bitmap index 126.

In a particular embodiment, data for the user profile may be retrieved from third party data sources, including but not limited to social networks. For example, the data may include, but is not limited to, demographic information associated with the user (e.g., a name, an age, a geographic location, a marital/family status, a homeowner status, etc.), social information associated with the user (e.g., social networking activity of the user, social networking friends/likes/interests of the user, etc.), and other types of data. In some examples, when a user profile is created, a data rights definition may automatically be created as well, where the data rights definition lists the user as the grantor and an entity associated with the measurement system 120 as the grantee. In some examples, the automatically created data rights definition may indicate specific data rights based on terms/conditions of use specified by the user or derived from the social networks or other data sources that were accessed to populate the user's profile.

The cloud-based storage 140 and the bitmap index 126 may be updated as additional event signals 110 are received (e.g., when additional users register with the media property, interact with the media property, etc.). When the measurement system 120 receives the query 150, the query execution module 124 may execute the query 150 based on a query execution plan that parallelizes execution and reduces/minimizes the amount of bit string data that is transferred between nodes during execution of the query 150.

In some examples, there may be interest in finding out more about the individual audience members in a segment, rather than merely "what are my top 50 segments." For example, it may be useful to, after identifying the top fifty segments for a property, retrieve a list of e-mail addresses of the users in each of the top fifty segments. As another example, it may be useful to compare the relative popularity of the segments for the property to a larger measurement universe that includes data for multiple properties. Relevant metadata that may be used to answer such queries may, in some examples, be stored as a part of the bitmap index 126 as custom internal metadata. Consequently, e-mail addresses for users (instead of or in addition to profile IDs) may be returned as a query result. Thus, including custom internal metadata in the bitmap index 126 may remove the need to access data structures or perform post-query external lookup operations in some cases. In some examples, data rights definitions associated with a data structure are stored as custom metadata within the data structure, as further described herein.

In some cases, the measurement system 120 may receive an access request 160. To illustrate, the access request 160 may specify a data structure (e.g., the bitmap index 126), where the data structure includes first data stored in a first portion of the data structure and second data stored in a second portion of the data structure. The first data may be shared with the requesting entity but the second data may not be shared with the requesting entity. In response to receiving the access request 160, the measurement system 120 may extract a first key from the request and may identify one of the data rights definitions 128 that is associated with the data structure. The identified data rights definition may indicate that the first data is shared with the requesting entity and may be associated with a second key. The measurement system 120 may compare first key to the second key. When the keys match, the measurement system 120 may grant the requesting entity access to the first data but not the second data. When the keys do not match, the measurement system 120 may deny the access request 160. In some embodiments, all read or write operation on a bitmap index include a key that is used to determine whether the read or write is authorized.

The system 100 of FIG. 1 may thus enable audience measurement and analysis based on data (e.g., event signals) received from various sources, and may further enable selectively sharing some, but not all, of the data stored in a data structure, such as the bitmap index 126 or a database table stored in the cloud-based storage 140. Event signals may be generated, for example, in response to user interactions with websites, web pages, audio items, video items, games, and/or text associated with various media properties. Further, the system 100 of FIG. 1 may enable real-time or near-real time execution of queries on the collected data. For example, the query execution module 124 may execute complex "top N" queries using the bitmap index 126 in real-time or near-real-time (e.g., within one hundred milliseconds).

Although one or more embodiments may be described herein in terms of audience measurement (e.g., the bit strings of the bitmap index 126 correspond to demographic information, brand affinities, and/or behaviors), it is to be understood that the present disclosure is not limited to audience measurement scenarios. In alternate embodiments, the bitmap index 126 may store healthcare-related data. For example, the described bitmap index may correspond to information associated with patients, medicines, medical staff (e.g., doctors, nurses, etc.) medical locations (e.g., clinics, hospitals, etc.), medical equipment, or any combination thereof. Accordingly, in such an embodiment, the event signals 110 may, in a particular example, identify a patient and correspond to a healthcare event (e.g., a visit to a doctor's office, a prescription being filled, a medical diagnosis, a medical treatment or medicine being administered, a reading from a medical sensor, etc.). Bit strings of the bitmap index 126 may additionally or alternatively correspond to medical attributes, such as medical history, allergy information, medication taken, etc. In some examples, the same location in each bit string may correspond to the same patient.

As another example, the bitmap index 126 may correspond to inventory or customers of a store. Bit strings of the bitmap index 126 may correspond to attributes of inventory, such as color, price, demand, number of an item "in stock," etc., and/or attributes of customers. The same location in each bit string may correspond to the same inventory item and/or the same customer.

As yet another example, in the financial industry, the same location in each bit string may correspond to the same investor, the same financial advisor, the same financial product, etc. Bit strings of the bitmap index 126, in a financial services context, can include demographic information, account information, investment information, or any combination thereof.

As yet another example, bit strings of the bitmap index 126 may correspond to data output by devices in an IoT environment, and the same location of each bit string may correspond to the same IoT device. When an IoT device includes a sensor, the data output by the IoT device can include a sensor reading. Alternatively, or in addition, the data output by an IoT device can indicate a communication transmitted to or received by the IoT device, a status of the IoT device (e.g., powering up, powering down, battery level, etc.), an event observed by the IoT device (e.g., motion detected by a motion sensor, pressure detected by a pressure sensor, etc.), or any combination thereof.

Figure 3:
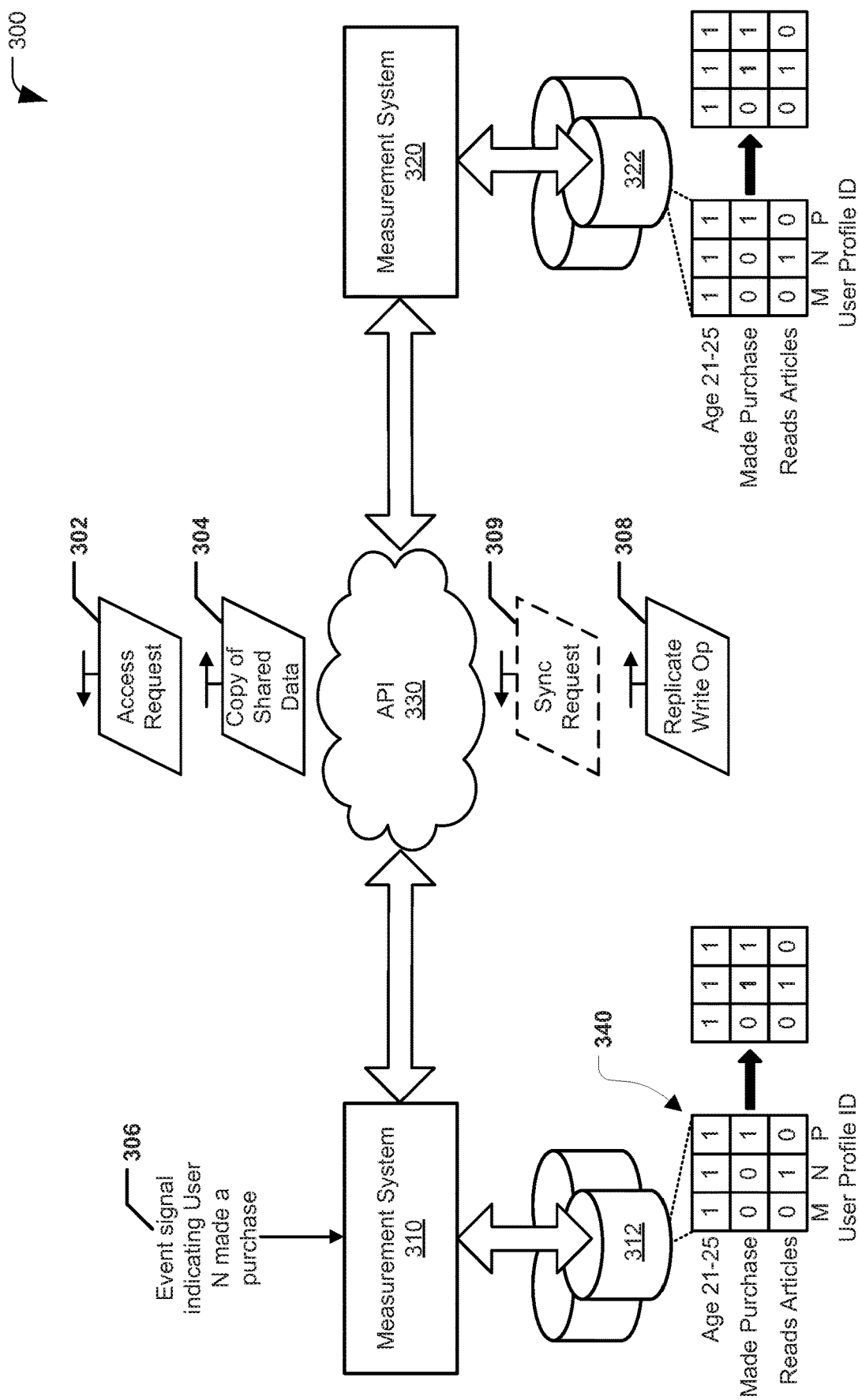
FIG. 3 is a diagram to illustrate another particular embodiment of a system that is operable to manage data rights and enable selective data sharing.

FIG. 3 illustrates an example of a system 300 that is operable to update shared data. In the example of FIG. 3, a first measurement system 310 is configured to communicate with a second measurement system 320 via an API 330. The first measurement system 310 is associated with first data storage 312, which may store one or more data structures, such as a bitmap index, a data table, etc. The second measurement system 320 is associated with second data storage 322.

During operation, the first measurement system 310 may generate data rights definitions, as described with reference to FIG. 1. The data rights definitions may indicate that data 340 (which may a portion of data stored in a data structure at the first data storage 312) is to be shared with the second measurement system 320 (or an entity associated therewith). In the illustrated example, the shared data 340 indicates whether three users having user profile identifiers (IDs) M, N, and P are in the age range 21-25, have made a purchase at a media property (e.g., website) and have read an article at the media property. The terms "profile ID" and "user ID" may be used interchangeably herein.

To access the shared data 340, the second measurement system 320 may send an access request 302 to the first measurement system 310. The access request 302 may correspond to an API call supported by the API 330 and may include a scoped API key. The first measurement system 310 may compare the scoped API key to a key stored in (or associated with) the data rights definition. If the keys match, the first measurement system 310 may send a copy 304 of the shared data 340 to the second measurement system 320 for storage in the second data storage 322.

In some cases, the shared data 340 may change after the copy 304 of the shared data 340 is provided to the second measurement system 320. For example, the first measurement system 310 may receive an event signal 306 indicating that user N made a purchase, resulting in a write operation that modifies a '0' value of a bit to a '1' value, as shown. In a particular embodiment, in response to performing or initiating the write operation of the bit at the first data storage 312, the first measurement system 310 may search data rights definitions to check if the bit being modified has been copied to any other places. If so, the first measurement system 310 may automatically send message(s) 308 to initiate a replication of the write operation at such places. In some aspects, the replication of the write is initiated via a push synchronization operation that is communicated to other computing devices that store a copy of the shared data 340. Alternatively, the replication of the write may be initiated via a pull synchronization operation or mechanism. To illustrate, the second measurement system 320 may send a synchronization request 309 to the first measurement system 310, and the first measurement system 310 may send the message 308 in response to the synchronization request 309. Push synchronization may enable near-real-time updates to copies of shared data, whereas pull synchronization may provide grantee control of updates (e.g., a data rights grantee may request synchronization on a periodic basis, such as once an hour, once a day, etc.).

Although FIG. 3 illustrates a synchronization of a grantor-side operation to the grantee-side, it is to be understood that this is for illustrative purposes only. If the second measurement system 320 has read/write access to the shared data 340 and the event 306 is received at the second measurement system 320, then the message 308 may be sent in the opposite direction (e.g., the bit indicating whether user N made a purchase may have been modified at the second data storage 322 before being modified at the first data storage 312).

FIG. 3 thus illustrates a system 300 that is operable to synchronize changes to shared data, e.g., to a portion of a data structure, to other locations. Such synchronization may occur using a pull-based mechanism or a push-based mechanism. When the data being shared is associated with user profiles, the system 300 may represent a networked customer relationship management (CRM) system. To illustrate, the system 300 may enable CRM systems associated with different entities to read, write, and share data regarding customers with each other.

Figure 4:
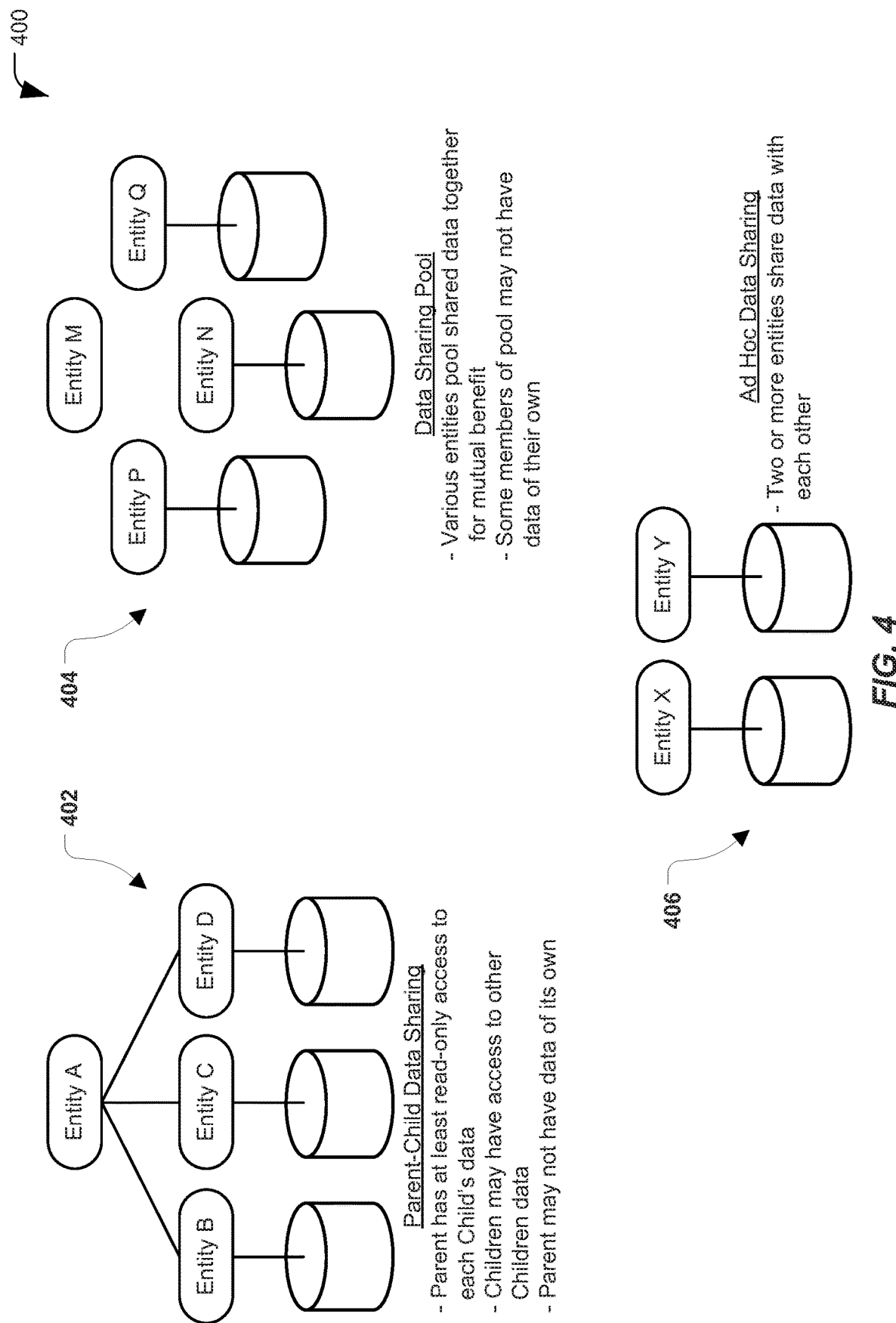
FIG. 4 is a diagram to illustrate particular embodiments of data sharing arrangements.

FIG. 4 illustrates examples of relationships between entities that may give rise to data sharing scenarios, as is generally designated 400. A first scenario 402 corresponds to parent-child data sharing. For example, Entity A may be a parent of Entities B, C, and D. To illustrate, Entity A may be a conglomerate parent corporation that includes subsidiaries in various industries. In such a scenario, the parent corporation may have access to the user profile data, event signals, etc. stored in bitmap indexes and/or database tables associated with each of the child entities. Data rights definition(s) used to implement the first scenario may list child entities B, C, and D as grantors and parent Entity A as a grantee. The parent entity may or may not have its own data, and if the parent entity has its own data, such data may or may not be shared with child entities. The child entities may or may not share data with other child entities.

A second scenario 404 corresponds to a data sharing pool in which various entities may pool shared data together. In some examples, some members of the data sharing pool may not contribute any data to the pool. To illustrate, in FIG. 4, entities M, N, P, and Q may be real estate firms that have at least read-only access to some but not all property listings (e.g., those property listings that are at least a month old) being offered by other real estate firms. Data rights definition(s) used to implement the second scenario 404 may list all of the members of the pools as grantors and may additionally list those members of the pool that are providing data as grantees.

A third scenario 406 corresponds to an ad hoc data sharing arrangement in which two or more entities share data with each other. The data sharing arrangement shown in FIG. 3, for example, may be such an ad hoc data sharing arrangement. The data rights definition 200 of FIG. 2 is an example of a data rights definition that may be used to implement an ad hoc sharing arrangement between two entities. It is to be understood, however, that the various operations described with reference to FIGS. 1-3 may be applicable in any of the scenarios 402-406.

As an example of an ad hoc data sharing arrangement, assume Entity X is an advertiser (e.g., a restaurant) and Entity Y is the owner of a news website. A first group of users may be known to the restaurant but not to the news website. For example, the first group of users may include users that have dined at or ordered takeout/delivery meals from the restaurant, users that have interacted with the restaurant via a social network, etc. A second group of users may be known to the news website but not to the restaurant. For example, the second group of users may include users that have registered at the news website, visited the news website and performed one or more actions (e.g., read news articles, watched video clips, etc.), interacted with an owning entity of the news website via a social network, etc. A third group of users may be known to both the restaurant and the news website. For example, the third group of users may include users that have both dined at the restaurant as well as registered at the news website.

Now assume that the restaurant places an advertisement on the news website. The restaurant may be interested in receiving information from the news website regarding users that viewed the advertisement, users the clicked on the advertisement, etc. To facilitate this, a data sharing agreement between the restaurant and the news website may be set up and embodied in a data rights definition. The data rights definition may list the news website as the grantor and the restaurant as the grantee. The data rights definition may further indicate that the restaurant has read-only access to the rows of the bitmap index (i.e., the segment/tile) corresponding to whether or not a user has viewed the advertisement and whether or not the user clicked on the advertisement. The data rights definition may further indicate that personally identifiable information is not being shared with the restaurant unless the user whose information is being shared was previously known to both the news website and the restaurant. To illustrate, the profile ID for the a user known to both entities may be the same in the CRM data at each of the entities, and personally identifiable information regarding a user of one entity may not be shared with the other entity unless the user's profile ID already exists in the other entity's CRM system (or in the other entity's bitmap index(es)).

Figure 5:
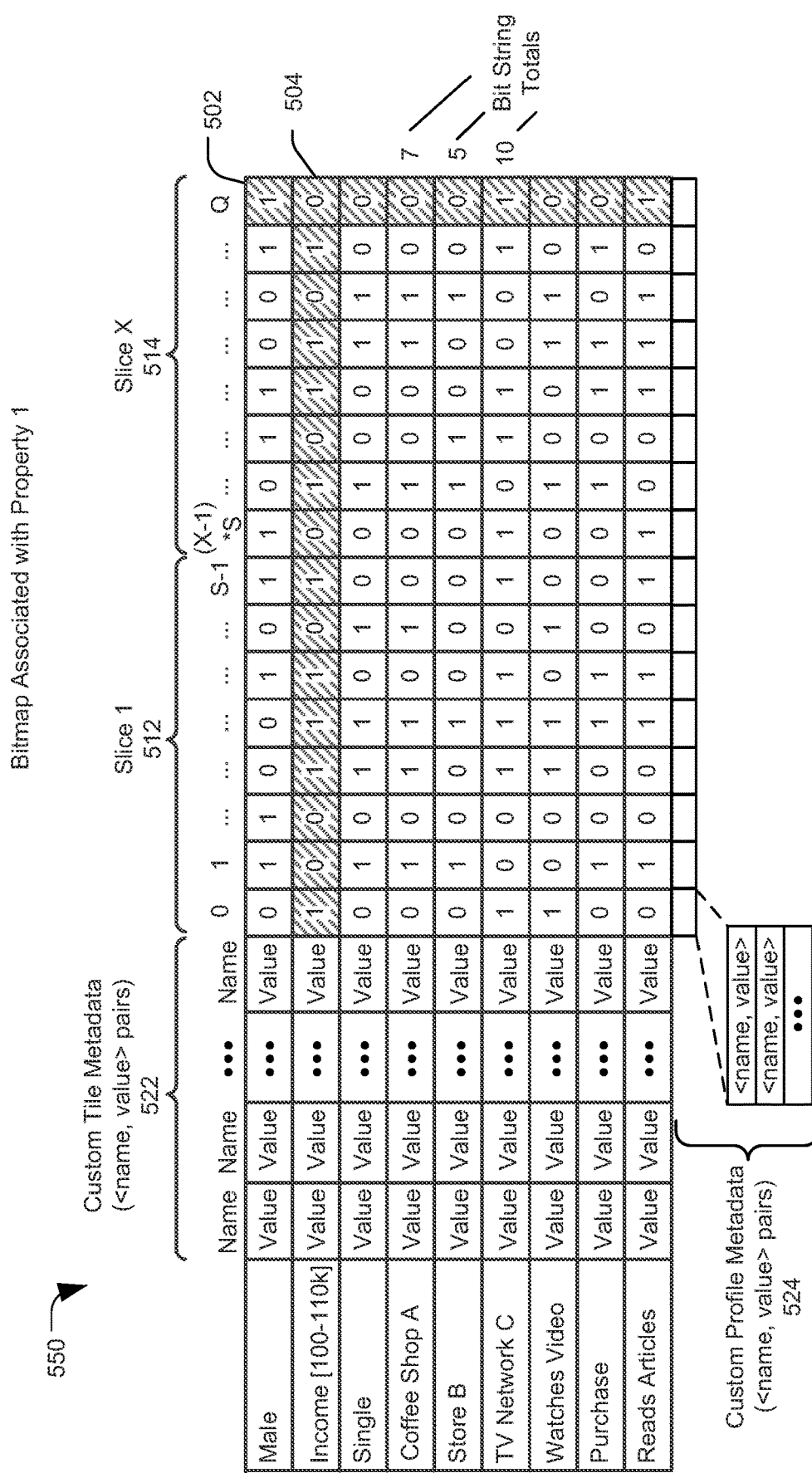
FIG. 5 is a diagram to illustrate a particular embodiment of a bitmap index.

Referring to FIG. 5, a particular embodiment of a bitmap index 550 is shown. In an illustrative embodiment, the bitmap index 550 is the bitmap index 126 of FIG. 1. The bitmap index 550 may correspond to a particular media property tracked by the measurement system 120 of FIG. 1. The bitmap index 550 stores a plurality of bit strings, which correspond to rows, or portions thereof, in the bitmap index 550. Each bit string represents a "tile," which in the example of FIG. 5 correspond to demographic signals, brand affinity signals, and/or behavior signals exhibited by the audience members. For purposes of illustration, the bitmap index 550 is shown as a grid, where each row 504 of the bitmap index 550 corresponds to a bit string. In FIG. 5, a bit string count is shown for the brand affinity bit strings. For example, the bit string for "Coffee Shop A" has a total of 7, indicating that 7 audience members have a brand affinity for "Coffee Shop A."

As described with reference to FIG. 1, the same location in each bit string may correspond to the same audience member (e.g., "profile" or user ID). Thus, each column 502 of the bitmap index 550 corresponds to a particular audience member. For example, a zero (0) at the intersection of the row 504 and the column 502 indicates that the user having a user ID equal to "Q" does not have an income in the range of $100,000-$110,000. It should be noted that the specific tiles shown in FIG. 5 for example only. Bit strings may be stored for more, fewer, and/or different tiles in alternative embodiments.

In a particular embodiment, each bit string in the bitmap index 550 is subdivided into "slices" (e.g., sub-strings). In the illustrated example, each slice includes S bits, where S is a positive integer. Thus, a first slice 512 of each bit string includes data related to audience members having IDs 0 to S−1. A last (e.g., $X^{th}$) slice 514 includes data related to audience members having IDs (X−1)*S to Q. When bit strings are subdivided into slices, different slices of the same bit string may be stored in different locations (e.g., storage nodes). A hashing algorithm, such as consistent hashing, may be used (e.g., during read operations, write operations, query execution, etc.) to identify locations of the slices of a bit string. The value of S, which represents the maximum length of each slice, may be set based on a desired query execution latency. In a particular embodiment, S is equal to 65,535 (e.g., each slice includes $2^{16}$ bits).

The bitmap index 550 may also include custom tile metadata 522 and custom profile metadata 524. In an illustrative example, such metadata 522, 524 is represented as <name, value> ("name-value") pairs, as shown in FIG. 5. As further described herein, when a query is executed on the bitmap index 550, the corresponding query results may include at least a portion of the metadata 522, 524. Moreover, as further described herein, in some embodiments, the custom tile metadata 522 and/or the custom profile metadata 524 may be used to store information regarding whether and in what fashion the corresponding tile(s) and profile(s) of the bitmap index 550 are being shared with other entities.

Figure 6:
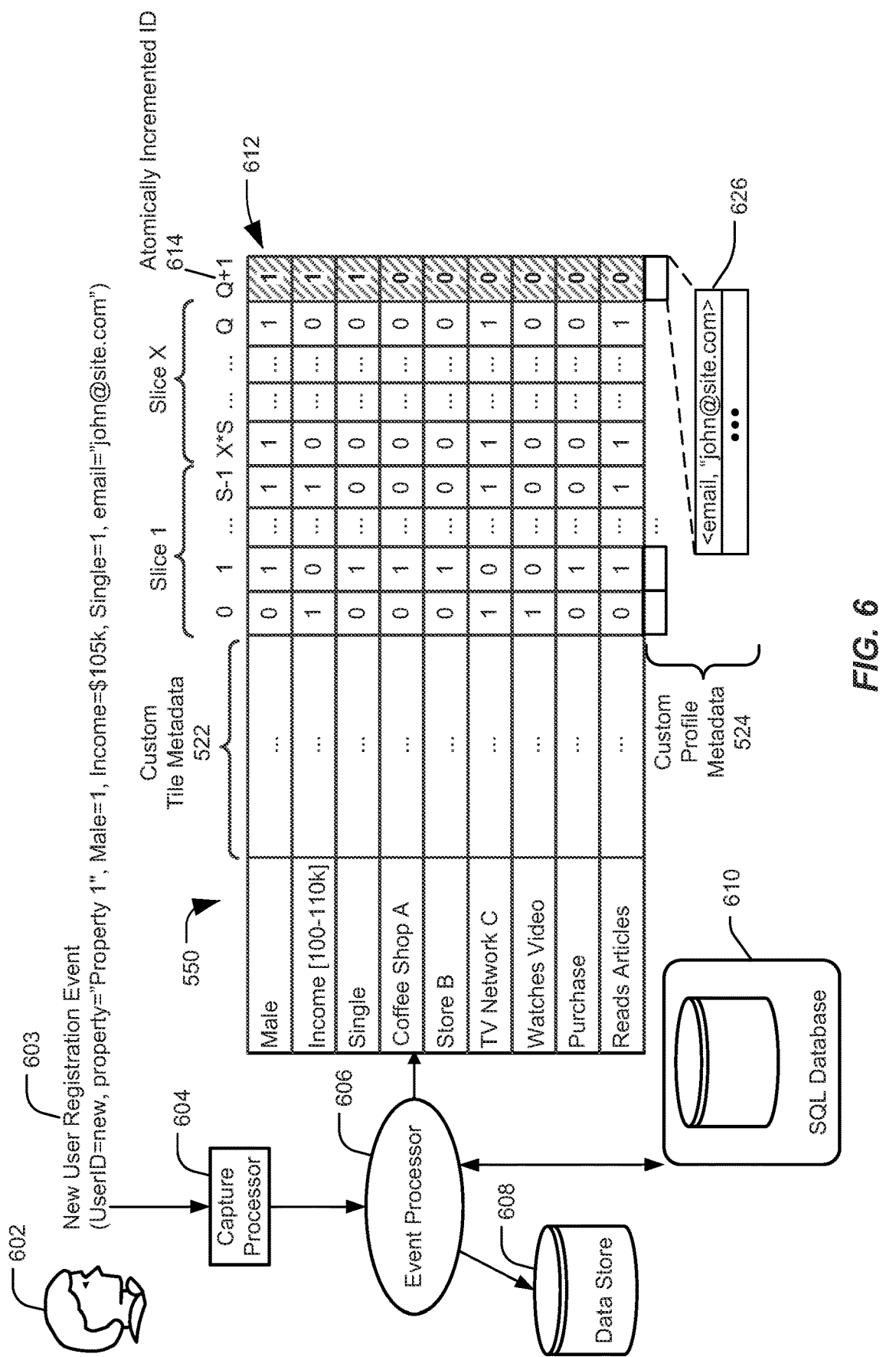
FIG. 6 is a diagram to illustrate a particular embodiment of a method of processing a registration event.

FIG. 6 illustrates an embodiment of adding a new user 602 to the bitmap index 550. In a particular embodiment, adding the new user 602 to the bitmap index 550 may involve a capture processor 604, an event processor 606, a data store 608, and a database (e.g., an illustrative structured query language (SQL) database 610). In an illustrative embodiment, the capture processor 604 and the event processor 606 correspond to the data processing module 122 of FIG. 1. The data store 608 and/or the SQL database 610 may correspond to the cloud-based storage 140 of FIG. 1.

During operation, the capture processor 604 may receive an event signal corresponding to a new user registration event 603 for the user 602. The event signal indicates that the user 602 is to be assigned a new user ID and is a new user for the media property "Property 1." The event signal also indicates (e.g., on the basis of retrieved social networking data and/or third-party data) that the user 602 is a male, has an income of $105,000, is single, and has an e-mail address of "john@site.com." In alternate embodiments, such information may be automatically retrieved by a measurement system after the new user registration event, as further described herein.

The capture processor 604 (which may implement a capture application programming interface (API)) may send the event signal to the event processor 606. Because the user 602 is a new audience member, the event processor 606 may generate and assign a new user ID to the user 602. For example, the event processor 606 may atomically increment a largest previously assigned user ID (e.g., Q) to generate a new user ID 614 (e.g., Q+1). In a particular embodiment, the event processor 606 requests the new user ID 614 from an atomic incrementer service (e.g., a web service). The event processor 606 may then store data corresponding to the event signal in the data store 608, the SQL database 610, and/or the bitmap index 550. For example, a new column 612 may be created in the bitmap index by storing a new $(Q+1)^{th}$ bit in each of the bit strings in the bitmap index. When allocating and storing data in the $(Q+1)^{th}$ column involves creating a new slice, the event processor 606 may automatically generate a new slice for each bit string of the bitmap index 550. The value of the $(Q+1)^{th}$ bit in the "Male," "Income [100-110 k]," and "Single" bit strings may be set to "1" based on the event signal. The value of the $(Q+1)^{th}$ bit in the remaining bit strings may be zero (e.g., a default value). In addition, a new <name, value> pair may be set in the custom profile metadata 524 for e-mail address of the newly added audience member, as shown at 626. In alternative embodiments, contact information other than or in addition to e-mail addresses may be included in the profile metadata 524.

In some examples, a data rights definition may automatically be established responsive to the new user registration event 603. For example, the data rights definition may list the user 602 as the grantor and "Property 1" (or an entity associated therewith) as the grantee. The data rights definition may indicate that whether the grantee has read-only or read-write access to the user's profile data, a validity time period for such rights, etc. In some examples, the data rights definition includes a key that is to be provided in subsequent event signals, such as when additional information regarding the user is received, for authentication purposes. To illustrate, a key may be generated for the user and may be provided to server(s) corresponding media properties, to servers corresponding to social networks, to devices associated with the user, etc., so that the key can be included when subsequent event signals are generated. In some examples, the data rights definition may "inherit" restrictions based on the terms of use associated with social networking websites or other data sources that were crawled to populate the bitmap index 550 for the user.

Figure 7:
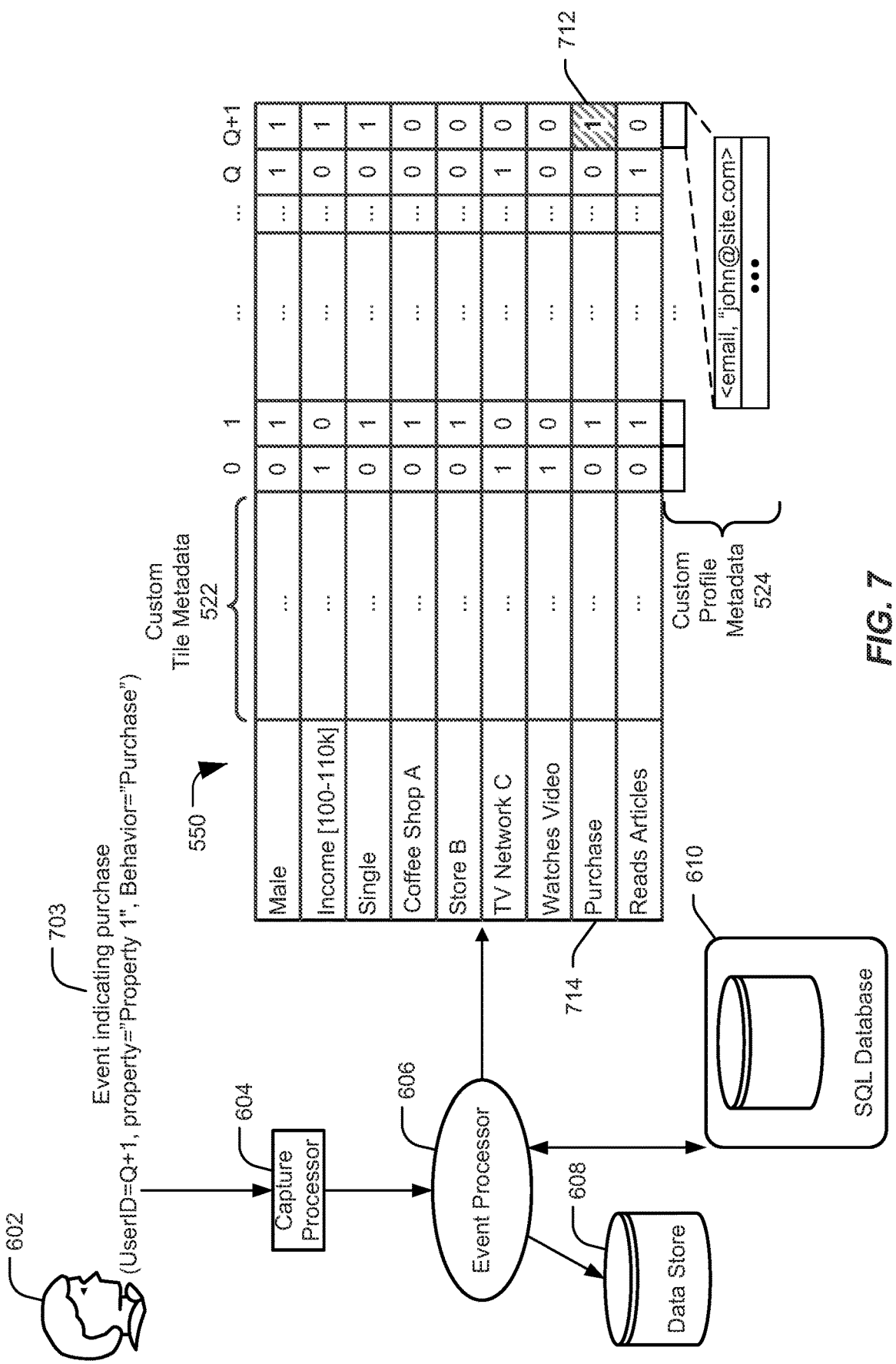
FIG. 7 is a diagram to illustrate a particular embodiment of a method of updating a bitmap index.

FIG. 7 illustrates a particular embodiment of updating the bitmap index 550. During operation, the capture processor 604 may receive an event signal 703 corresponding to updated information for the user 602. In the illustrated example, the event signal 703 is generated based on the user 602 making a purchase on the media property. The event processor 606 may receive the event signal 703 and determine which row(s) and column(s) of the bitmap index 550 are affected by the event signal 703. In the illustrated example, the event processor 606 determines that the event signal 703 will cause the value of the $(Q+1)^{th}$ bit 712 of a "Purchase" bit string 714 to be set to "1." The event processor 606 may also update the data store 608 and/or the SQL database 610 based on the received event signal 703. In some examples, the event signal 703 may include a key that is compared with a data rights definition associated with the user, for authentication purposes, before the event processor updates the data store 608, the SQL database 610, and/or the bitmap index 550.

Figure 8:
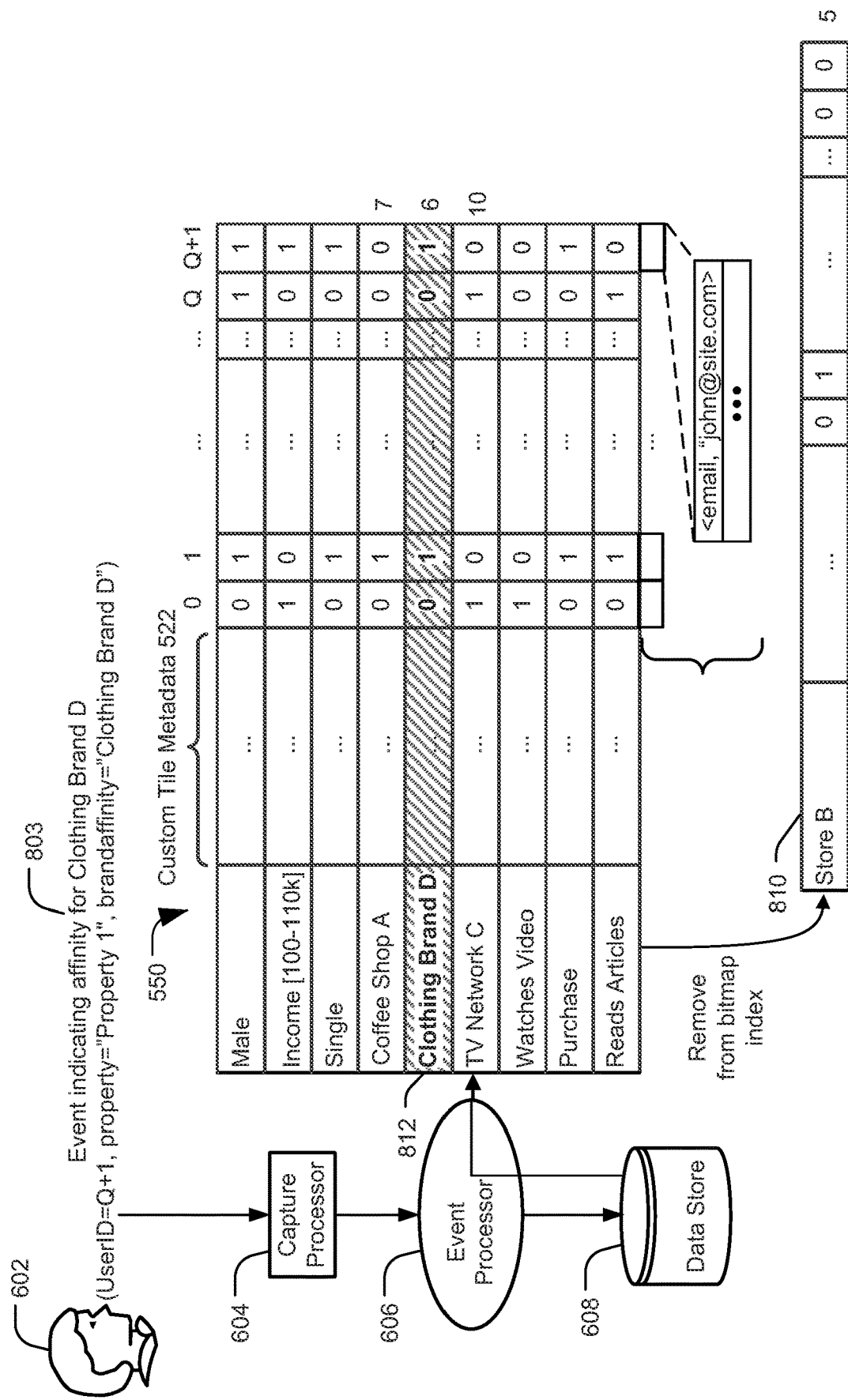
FIG. 8 is a diagram to illustrate another particular embodiment of a method of updating a bitmap index.

As described with reference to FIG. 1, in some embodiments, the bitmap index 550 includes bit strings for fewer than all of the attributes/tiles being tracked. For example, although all demographic and/or behavioral tiles may be stored in the bitmap index 550, bit strings for only the top N brands may be included in the bitmap index 550, where N is an integer greater than or equal to one. In such embodiments, a received event signal may cause a particular tile to become elevated into or fall out of the top N tiles. FIG. 8 illustrates a particular embodiment of updating the bitmap index 550 responsive to an event signal.

For ease of illustration, the bitmap index 550 is depicted as storing three brand affinity bit strings (i.e., N=3). Initially, the three brands may be "Coffee Shop A," "Store B," and "Television Network C." The brand affinity counts for the three brands are 7, 5, and 10 audience members, respectively. Brand affinity data for additional brands (e.g., brands outside the top N brands) may be stored in the data store 608.

A received event signal 803 may indicate that the user 602 has an affinity for "Clothing brand D." Upon receiving the event signal 803, the event processor 606 may determine that a brand affinity bit string for "Clothing Brand D" is not stored in the bitmap index 550. Thus, the event processor 606 may store data for the event signal 703 in the data store 608. The event processor 606 (or a background process or thread) may determine that because of the event signal 803, "Store B" (which has a count of 5) has fallen outside of the top N brands and that "Clothing Brand D" (which now has a count of 6) has become elevated into the top N brands. In response to the determination, a bit string 810 for "Store B" (including any associated tile metadata 522) may be replaced in the bitmap index 550 with a bit string 812 for "Clothing Brand D" (along with any associated tile metadata 522, which in some examples may include data rights information associated with the bit string for "Clothing Brand D," i.e., whether and in what fashion user affinities for "Clothing Brand D" is shared with other entities).

Figure 9:
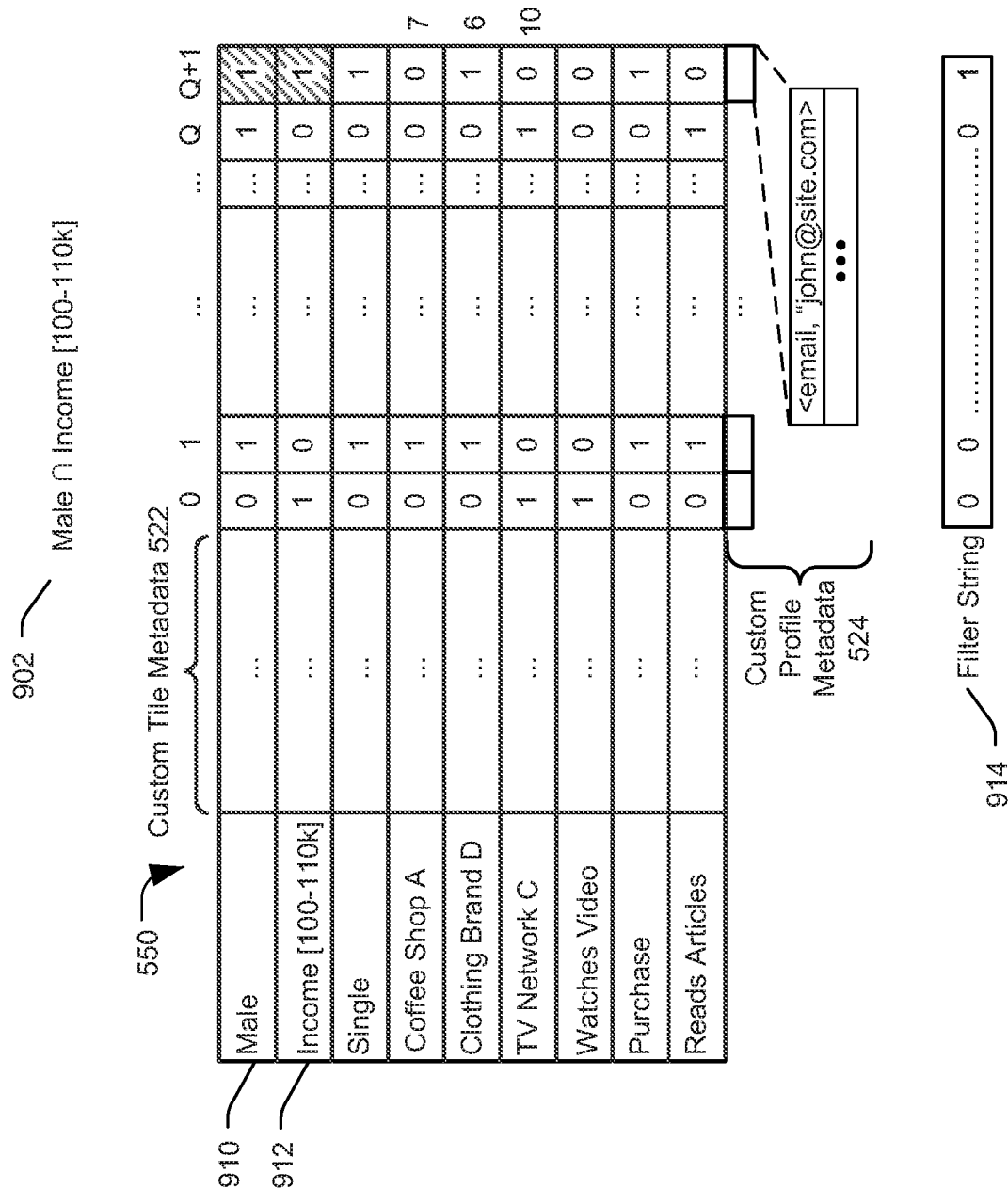
FIG. 9 is a diagram to illustrate a particular embodiment of a method of using a bitmap index during execution of a query.

FIG. 9 illustrates a particular embodiment of executing (e.g., resolving) a query 902 using the bitmap index 550. The query 902 may be received and executed by the query execution module 124 of FIG. 1. The result of executing the query 902 is another bit string 914, referred to herein as a "filter string." In the illustrated example, the query 902 corresponds to an intersection (logical AND) operation between the "Male" and "Income [100-110 k]" demographic properties (i.e., corresponds to the question "Which of my audience members is male and has a household income between $100,000 and $110,000?"). Thus, the filter string 914 may correspond to a custom segment of an audience of a particular property that is associated with the bitmap index 550. The custom audience segment may correspond to an aggregation of audience segments generated using one or more set operations, such as logical AND operations and logical OR operations.

Resolving the query 902 may including ANDing each bit string location (i.e., each user) of a "Male" bit string 910 with a corresponding location of an "Income [$100-110 k]" bit string 912, as shown. When both corresponding locations contain a "1," the corresponding location of the filter string 914 is set to 1. At the conclusion of the AND operations, the filter string 914 corresponds to a custom audience segment of men who earn $100,000-$110,000.

Figure 10:
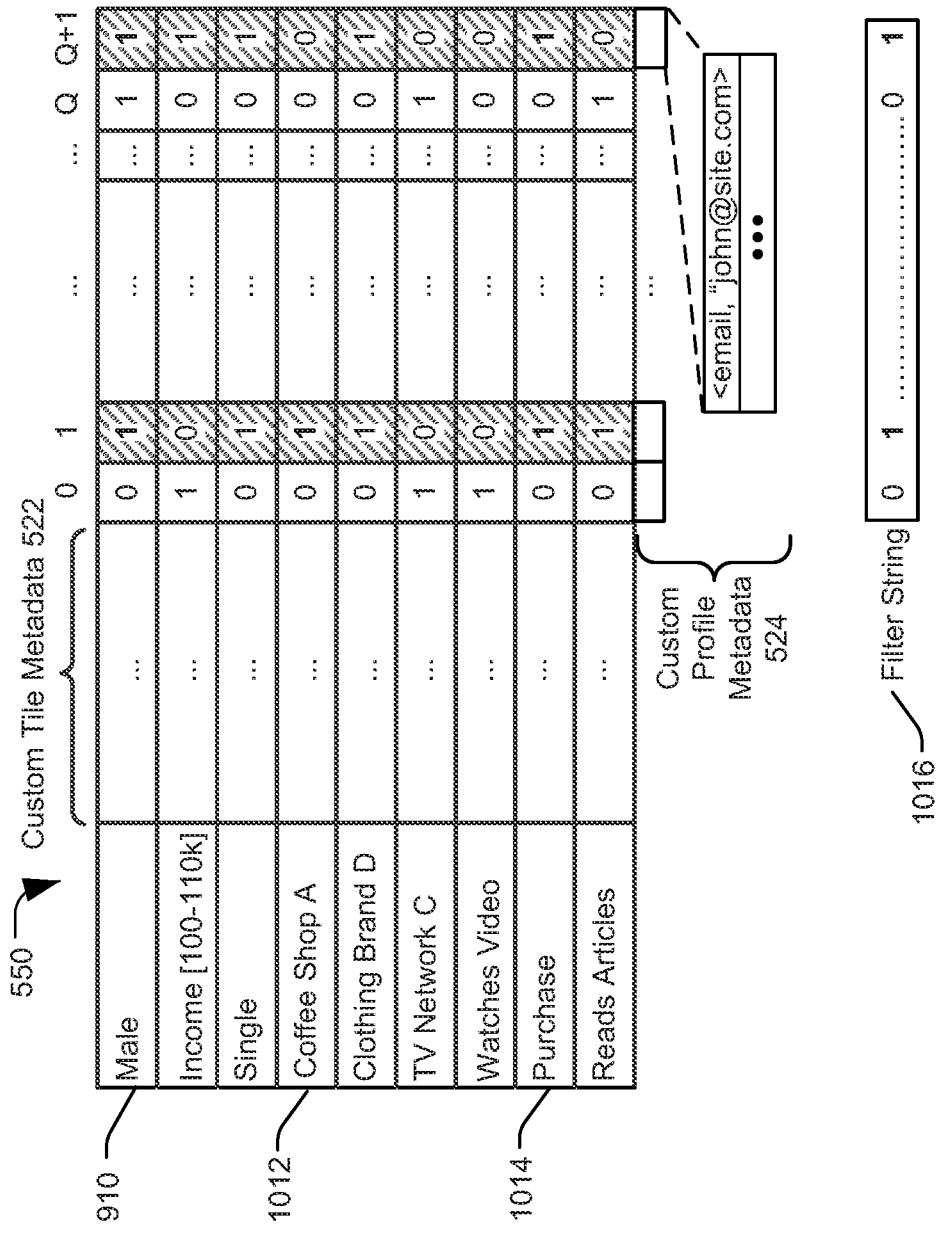
FIG. 10 is a diagram to illustrate another particular embodiment of a method of using a bitmap index during execution of a query.

In a particular embodiment, the filter string 914 is stored and available for use during execution of subsequent queries. The filter string 914 may also be used to query the data store 608 (e.g., cloud-based storage) or the SQL database 610 (e.g., a user profile database) regarding the custom audience segment. It should be noted that while the illustrated query 902 calls for a single set operation to generate the filter string 914, the described techniques may be used with more complex queries that involve any number of union operations, intersection operations, and/or count operations. For example, FIG. 10 illustrates a particular embodiment of resolving a (more complex) second query 1002 to generate a second filter string 1016. In FIG. 10, the query 1002 is a top Z brand affinities query (where Z is a positive integer).

The query 1002 requests identification of audience members that are male and that like "Coffee Shop A" or have made a purchase on the media property. The filter string 1016 may be generated by ORing a "Coffee Shop A" bit string 1012 with a "Purchase" bit string 1014 to generate an intermediate result string (not shown). The filter string 1016 may be generated by ANDing the "Male" bit string 910 with the intermediate result string. The audience members having a "1" in the filter string 1016 represent the audience members who are male and either have a brand affinity for "Coffee Shop A" or have made a purchase. In a particular embodiment, the filter string 1016 may be stored and used during execution of subsequent queries. For example, to answer the question "What are the top 50 brands for men in my audience that either have an affinity for Coffee Shop A or have made a purchase?" the filter string 1016 may be generated. The filter string 1016 may be ANDed with each of the brand affinity bit strings to generate result strings. Count operations may be performed on the result strings and the 50 brand affinities with the highest counts may be returned in response to the question.

As another example, to answer the query "What are the e-mail addresses for men in my audience that either have an affinity for Coffee Shop A or have made a purchase," after the filter string 1016 is generated, e-mail addresses may be determined, based on the custom profile metadata 524, for each user whose corresponding value in the filter string is "1." To illustrate, because the user having the ID Q+1 has a value of "1" in the filter string 1016, the e-mail address "john@site.com" is returned as a result for the query. As another example, to answer the query "What data rights are established for men in my audience that either have an affinity for Coffee Shop A or have made a purchase," after the filter string 1016 is generated, such data rights may be determined based on information stored in the custom profile metadata 524 for each user whose corresponding value in the filter string is "1."

It will be appreciated that during query execution, the AND/OR operations performed on bit strings are performed one bit at a time, and the result of an operation on any single bit location does not impact the result of the operation on any other bit location. Thus, query execution may be parallelized. For example, when slices of the bit strings are stored at different network nodes, performing an operation with respect to bit strings may be parallelized into performing the operation with respect to individual slices at individual nodes. To determine where and in what order such parallel operations should be performed, a query execution module may generate a query execution plan.

Figure 11:
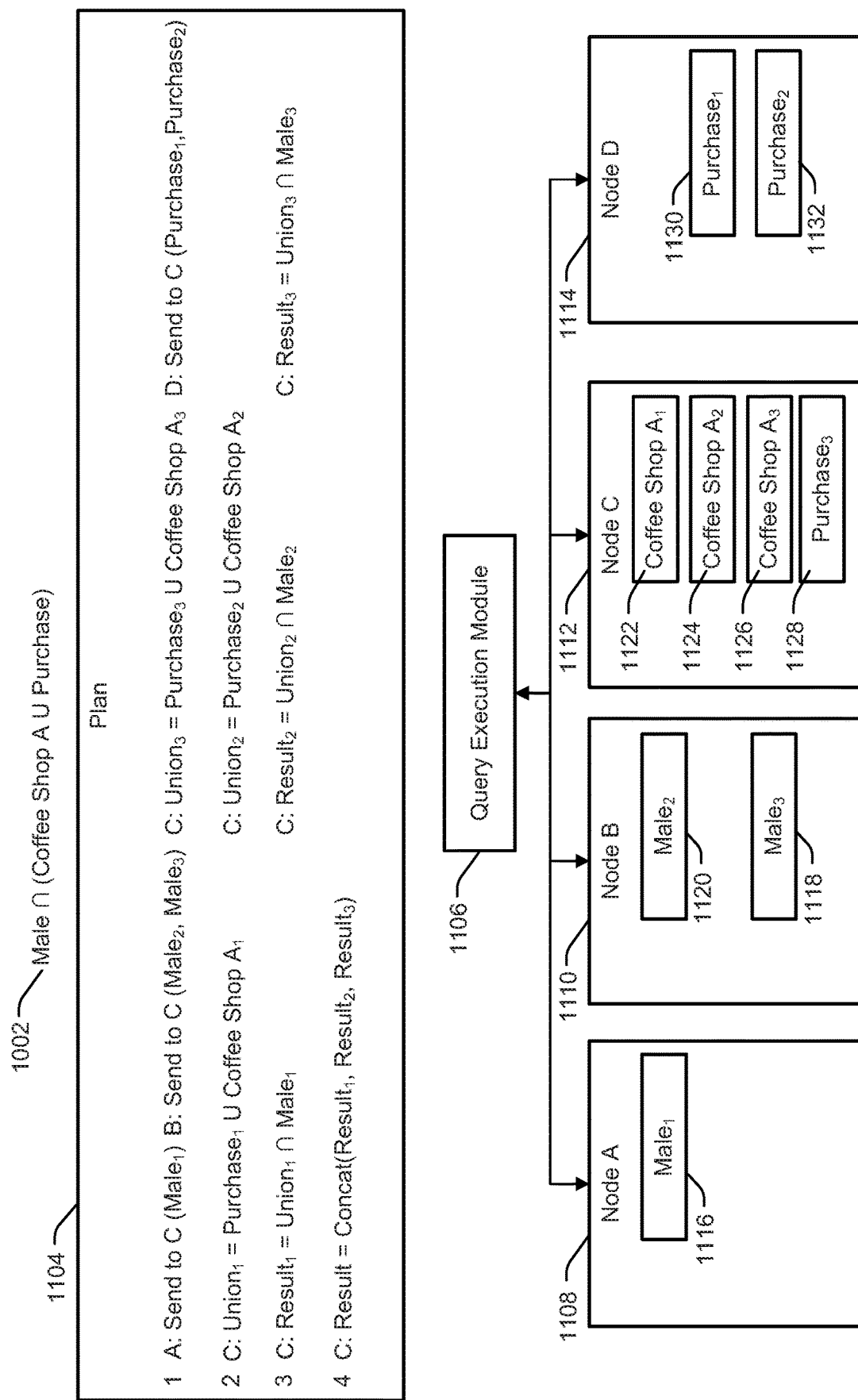
FIG. 11 is a diagram to illustrate a particular embodiment of a method of generating a query execution plan corresponding to the query of FIG. 10.

For example, FIG. 11 illustrates a particular embodiment of generating of a query execution plan 1104 to resolve the query 1002 of FIG. 10. Upon receiving the query 1002, a query execution module 1106 may generate a query execution plan 1104. In a particular embodiment, because data transfers between nodes may represent a bottleneck, the query execution plan 1104 may be generated such that data transfers are reduced/minimized. In a particular embodiment, the query execution module 1106 is part of one of the nodes 1108-1114. Alternately, the query execution module 1106 may be part of a separate node (e.g., a load-balancing node).

For example, the query execution module 1106 may determine that resolution of the query 1002 of FIG. 10 involves performing operations on the "Male" bit string, the "Coffee Shop A" bit string, and the "Purchase" bit string. In the illustrated example, each of the bit strings has three slices. A first slice 1116 of the "Male" bit string, designated $Male_1$ is stored on Node A 1108. A $Male_2$ slice 1118 and a $Male_3$ slice 1120 are stored on Node B 1110. Coffee Shop $A_1$, Coffee Shop $A_2$, Coffee Shop $A_3$, and $Purchase_3$ slices 1122, 1124, 1126, and 1128 are stored on Node C 1112. $Purchase_1$ and $Purchase_2$ slices 1130 and 1132 are stored on Node D 1114.

In an illustrative embodiment, each slice corresponds to a data object that includes a bit array, an array of profile IDs corresponding to the bits in the bit array (or alternatively, a starting profile ID and an ending profile ID), a tile ID, a slice ID, an array of <name, value> pairs for tile metadata (which may include <name, value> pairs regarding data rights for various tiles), and an array of <name, value> pairs for profile metadata (which may include <name, value> pairs regarding data rights for various user profiles). Thus, when the following description refers to copying or moving a slice, the various IDs and metadata stored in conjunction with the slice may also be copied or moved.

The query execution plan 1104 identifies operations and at what nodes are to perform the operations. For example, the query execution plan 1104 indicates that in a first step, Node C 1112 is to perform a union (OR) operation between Coffee Shop $A_3$ slice 1126 and the $Purchase_3$ slice 1128 to generate an intermediate result slice $Union_3$. In parallel, Node A 1108 is to transfer a copy of the $Male_1$ slice 1116 to Node C 1112 and Node B 1110 is to transfer copies of the $Male_2$ slice 1118 and the $Male_3$ slice 1120 to Node C 1112. Node D is to transfer copies of the $Purchase_1$ slice 1130 and the $Purchase_2$ slice 1132 to Node C 1112.

In a second step, Node C 1112 performs two operations in parallel: ORing the $Purchase_1$ slice 1130 and the Coffee Shop $A_1$ slice 1122 to generate an intermediate result slice $Union_1$, and ORing the $Purchase_2$ slice 1132 and the Coffee Shop $A_2$ slice 1124 to generate an intermediate result slice $Union_2$.

In a third step, Node C 1112 performs three operations in parallel to generate three intermediate bit strings. The first intermediate bit string $Result_1$ is generated by ANDing the $Union_1$ slice with the $Male_1$ slice. The second intermediate bit string $Result_2$ is generated by ANDing the $Union_2$ slice with the $Male_2$ slice. The third intermediate bit string $Result_3$ is generated by ANDing the $Union_3$ slice with the $Male_3$ slice. In a fourth step, Node C concatenates the $Result_1$, $Result_2$, and $Result_3$ bit strings to generate the filter string 1016 of FIG. 10.

FIG. 11 thus illustrates generation of a query execution plan for a query. In a particular embodiment, the query execution plan is generated prior to performing any set operations. The query execution plan may be generated so as to increase the number of parallel operations and reduce the number of bit string (or slice) transfers between nodes, which may result in improved query execution latency.

Figure 12:
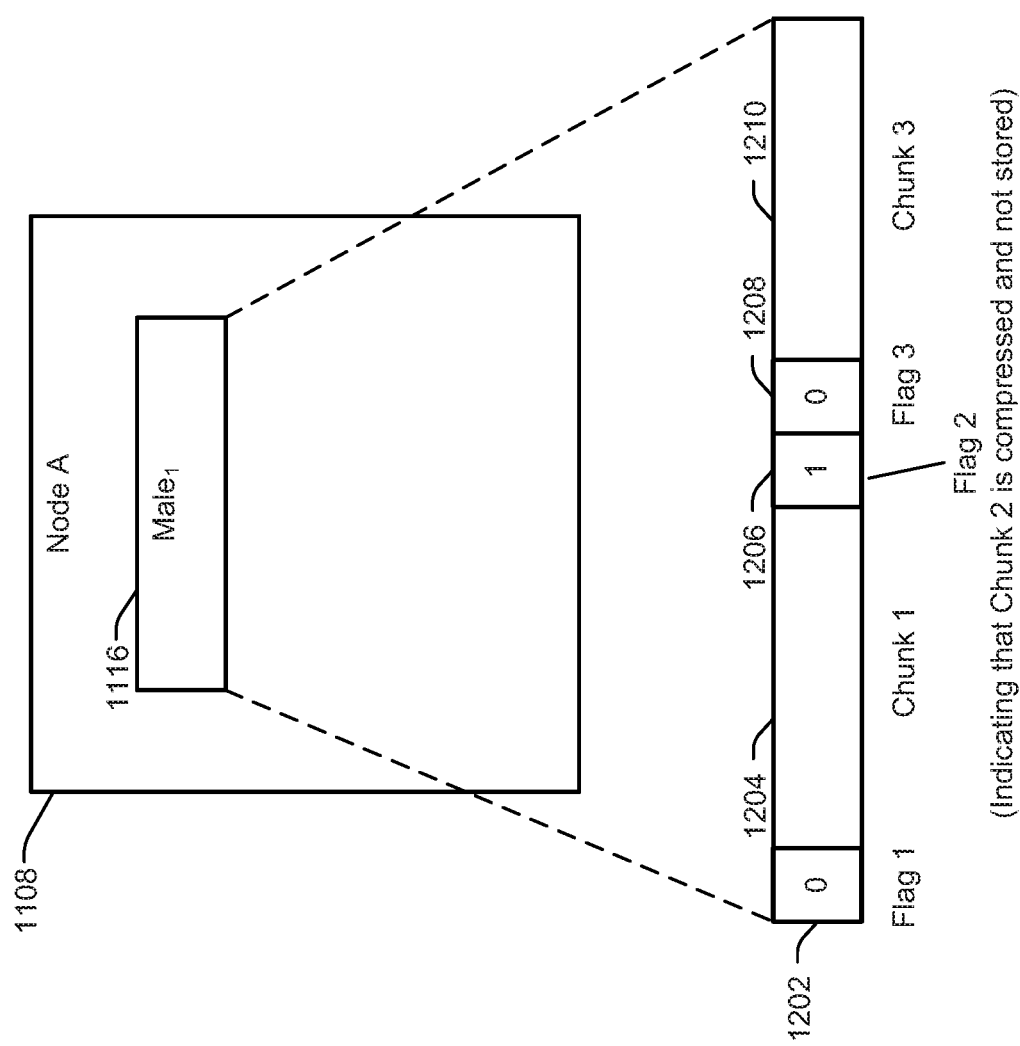
FIG. 12 is a diagram to illustrate a particular embodiment of a method of compressing and storing a bit string of a bitmap index.

In the foregoing description, bit strings are described as being subdivided into slices. For example, each slice may include 64 kibibits (1 kibibit=$2^{10}$ bits=1,024 bits). In a particular embodiment, slices may be further divided into "chunks." For example, chunks may be up to 2 kibibits in length (e.g., each slice is subdivided into 32 chunks). To reduce the amount of space occupied by bit strings of a bitmap index, chunks may be stored in a compressed fashion. For example, FIG. 12 illustrates a particular embodiment of compressing and storing data of a bitmap index. In particular, FIG. 12 depicts Node A 1108 of FIG. 11, which stores the $Male_1$ slice 1116. The (bit array of) $Male_1$ slice 1116 may be compressed in accordance with various compression schemes. In the illustrated compression scheme, chunks that have only zeroes are not stored. Chunks that include a one are stored. A flag corresponding to each chunk is stored. If a flag has a value of zero, the corresponding chunk is stored in its entirety. For example, a first flag 1202 and a third flag 1208 have a value of zero, indicating that corresponding first chunk 1204 and third chunk 1210 are stored at Node A 1108. If a flag has a value of one, the corresponding chunk is "compressed" by not being stored. For example, a second flag 1206 has a value of one, indicating that a corresponding second chunk includes only zeroes and is not stored. During queries, the second chunk may be dynamically generated by introducing zeroes (e.g., 2,048 zeroes) between the first chunk 1204 and the third chunk 1210.

While FIG. 12 illustrates one example of a compression scheme, in alternate embodiments, different compression schemes may be used. Further, data for the compression scheme may be stored in different places. For example, the chunks 1204 and 1210 may be stored at Node A 1108, and the flags 1202, 1206, and 1208 may be stored in a different location (e.g., as part of a hash table that is used to identify where slices/chunks of a bit string are stored).

Figure 13:
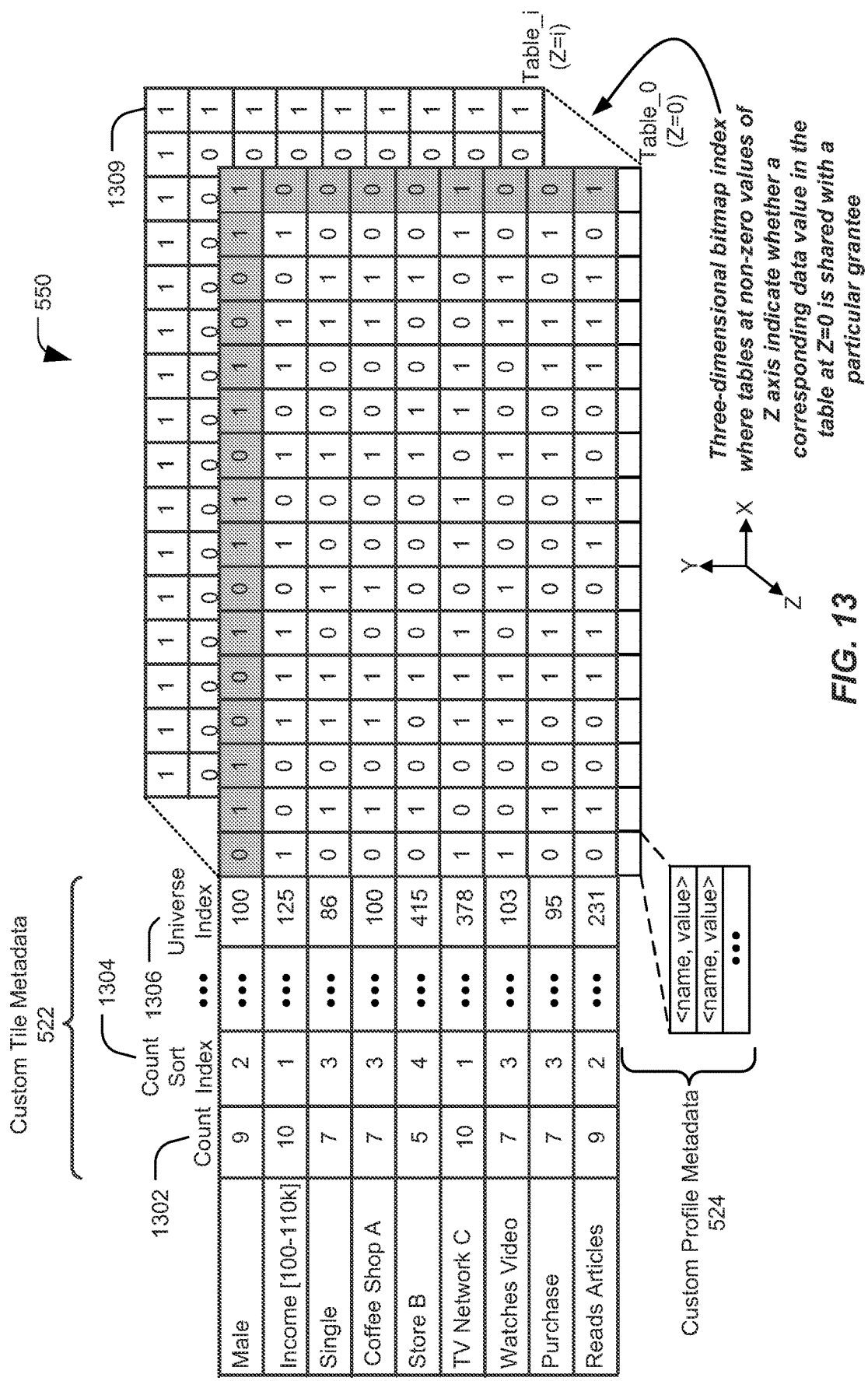
FIG. 13 is a diagram to illustrate a particular embodiment of an multidimensional bitmap index including an internally stored data rights definition.

FIG. 13 illustrates an example in which the bitmap index 550 is three-multidimensional and includes internal storage of data rights information. To illustrate, the values at each X,Y coordinate of a Table_0 of the bitmap index 550, corresponding to Z=0, may be based on received event signals, as described with reference to FIGS. 1-8. That is, Table_0 may represent the "actual" data values of the bitmap index 550. The remaining tables of the bitmap index, such as Table_i for Z=i, indicate whether each bit in the Table_0 is shared with a corresponding data rights grantee. For example, the values stored in the top row and the right-most column of Table_i in FIG. 13 are "1" s. Accordingly, the values in the "Male" bit string and for the user represented by the right-most column of Table_0 may be shared with an entity corresponding to Table_i. Similarly, values stored in the bitmap index 550 within tables for other non-zero values of Z may indicate whether data in Table_0 is shared with other entities.

In some examples, the custom tile metadata 522 and/or the custom profile metadata 524 stored in the bitmap index 550 for non-zero values of Z may include additional data rights information. For example, the custom tile metadata 522 and/or the custom profile metadata 524 may indicate whether read-only access or read-write access is being granted, a data sharing validity time period, and/or a key that is to be provided by the grantee in access requests for the shared data stored in the bitmap index 550.

When an access request is received by a computing device that stores or that has access to the multidimensional bitmap index 550, the computing device may determine whether the requestor has been granted any data rights for the bitmap index 550, i.e., a table for a non-zero value of Z corresponds to the requestor. If so, the computing device may examine the table to compare a key included in the access request to a key included in the table. If the keys match and the table further indicates that the requestor has access to the X,Y coordinates specified in the request, the computing device may grant the requestor access to the data stored at the specified X,Y coordinates in Table 0. FIG. 13 thus illustrates an example in which a data rights definition that enables selective sharing of a bitmap index (or a portion thereof) is integrated into the bitmap index itself.

FIG. 13 also illustrates an example of storing multiple sortable metadata items in the bitmap index 550. In particular, the custom tile metadata 522 includes a count 1302, a count sort index 1304, and a universe index 1306 for each bit string 1304. Thus, in a particular embodiment, if slices of a bit string are stored in distributed fashion, then data regarding the count 1302, the count sort index, and the universe index 1306 may be stored along with each slice.

In accordance with the present disclosure, multiple sortable metadata items may be included in the bitmap index 550. In the example of FIG. 13, the count 1302 corresponds to the count of "1" values in each bit string. In some examples, the count 1302 for an individual slice may be the count of "1" values in the slice rather than the bit string as a whole. Alternatively, the total count 1302 may be stored along with each slice. The count sort index 1304 may enable the bitmap index 550 to be quickly sorted by the count 1302. When the bitmap index 550 is sorted by the count 1302, the bit strings for "Income 100-110 k" and "TV Network C" will rise to the top; therefore those bit strings have count sort indexes of 1. Adding sort indexes to the bitmap index 550 may enable the bitmap index to function as a cache that is concurrently sorted by multiple individual, custom sorting parameters (e.g., count, universal index, etc.). As data in the bitmap index changes, the sort indexes can be updated without having to relocate bit strings higher or lower within the bitmap index.

In an illustrative embodiment, the universe index 1306 is based on a comparison of a popularity of a tile with respect to a media property (e.g., website) and a popularity of the tile with respect to a larger measurement universe that includes multiple media properties (e.g., websites). To illustrate, a measurement system, such as the measurement system 120 of FIG. 1, may collect data regarding audiences of a large number of media properties. If a media property owner opts-in to aggregate data metrics, then the universe index 1306 may be generated in the bitmap index for the media property. In the example of FIG. 13, a universe index of 100 indicates that the corresponding tile is equally popular in the measurement universe as it is for the individual media property. If the tile is less popular for the media property than for the measurement universe, the universe index has a value of less than 100. If the tile is more popular for the media property than for the measurement universe, the universe index has a value of more than 100. In the illustrated example, "Store B" has a relatively low count of 5 but a large universe index of 415, indicating that the media property has a much larger proportion of "Store B" fans than the measurement universe as a whole. Based on this information, the owner of the media property may tailor content and/or marketing campaigns with information related to "Store B," in the hopes of turning their media property into a "go-to" Internet location for information about "Store B."

Although not shown in FIG. 13, it is to be understood that various other types of tile and/or profile metadata may be stored in the bitmap index 550. For example, the bitmap index 550 includes a category for bit strings. To illustrate, each of multiple brands of beer, wine, and spirits may have "alcoholic beverages" listed as a category. The category metadata may enable determining a custom composite segment that includes each of the beer, wine, and spirit brands. For example, although individual brands may have low counts, the custom segment for alcoholic beverages may have a large enough count to warrant marketing attention. Such category metadata may also enable querying the bitmap index 550 using "alcoholic beverage" rather than having to OR together individual beer, wine, and spirit brands.

As described above, a data rights definition may, in some aspects, may representative of or may be considered as an agreement between a grantor and a grantee. In a particular embodiment, such agreements may be processed to determine a monetary value of the agreements. To illustrate, the monetary value of a data rights definition may be a function of one or more properties associated with the grantor (e.g., grantor market cap, grantor reputation or influence, number of social network followers, etc.), one or more properties associated with the grantee (e.g., grantee market cap, grantee reputation, number of social network followers, etc.), one or more properties of the data being shared (e.g., number of tiles/segments being shared, number of user profiles being shared, etc.), whether the sharing provides for read-only or read-write access, whether personally identifiable information is being shared, the duration that the data rights definition is valid, etc. By determining a monetary values associated with the data rights definitions, an entity may be able to determine reasonable fees to be paid/collected for data sharing, a payment to pay to a user to incentivize the user to grant access rights to their profile information, etc.

Figure 14:
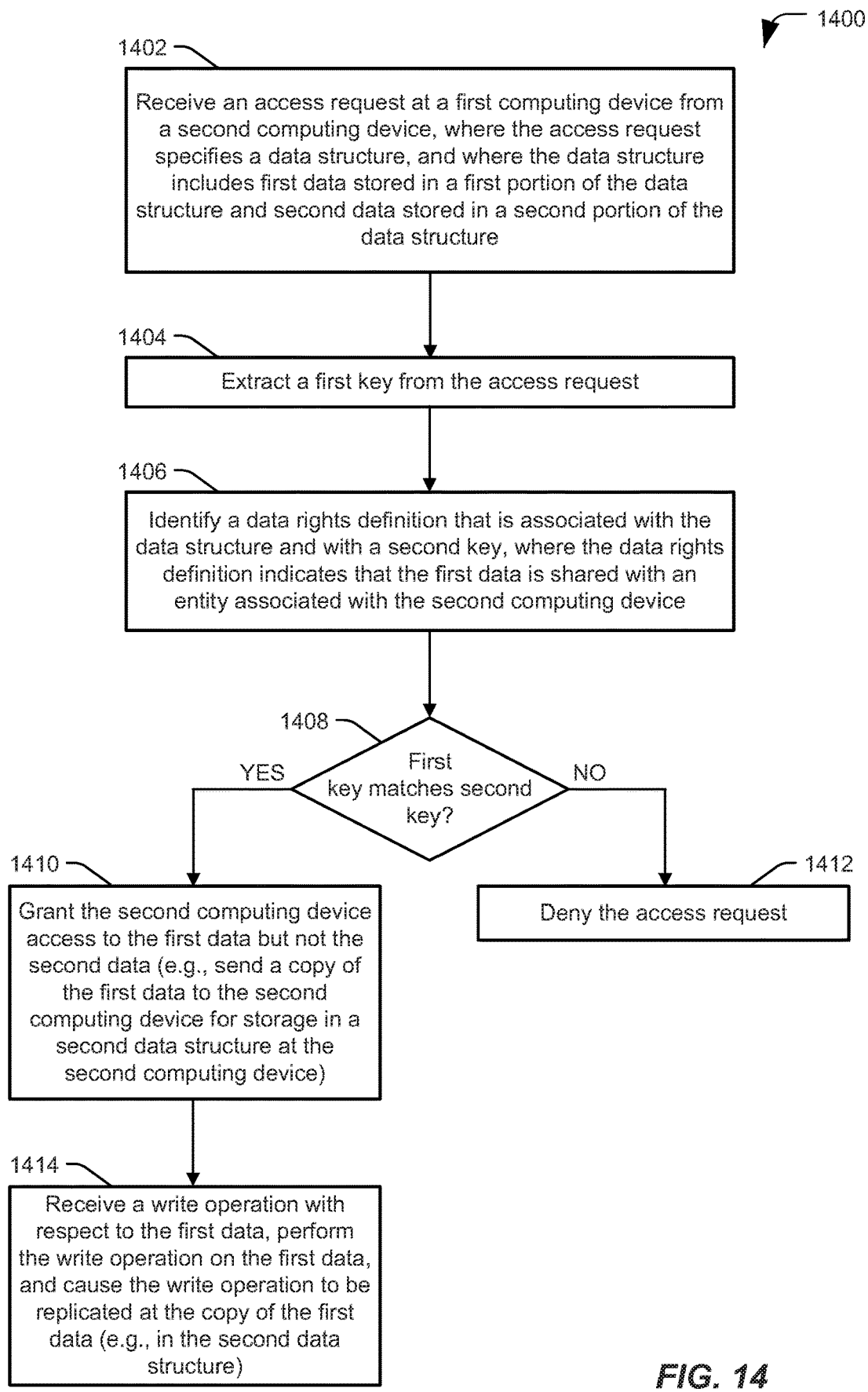
FIG. 14 is a flowchart to illustrate a particular embodiment of a method of operation in accordance with the present disclosure.

Referring to FIG. 14, a particular embodiment of a method 1400 of operation is shown. In an illustrative embodiment, the method 1400 may be performed by a computing device having a processor, such as a computing device included in the measurement system 120 of FIG. 1.

The method 1400 includes receiving an access request at a first computing device from a second computing device, at 1402. The access request specifies a data structure, where the data structure includes first data stored in a first portion of the data structure and second data stored in a second portion of the data structure. For example, in FIG. 3, the first measurement system 310 may receive the access request 302 from the second measurement system 320, where the access request specifies the shared data 340.

The method 1400 also includes extracting a first key from the access request, at 1404, and identifying a data rights definition that is associated with the data structure, at 1406. The data rights definition is further associated with a second key and indicates that the first data is shared with an entity associated with the second computing device. For example, in FIG. 3, the first measurement system 310 may extract a key from the received access request 302 and may identify a data rights definition associated with the shared data 340, where the data rights definition includes a second key. For example, the first measurement system 310 may search a repository of data rights definitions for data rights definition(s) that list the entity associated with the second computing device as a grantee, that lists the particular data structure or portion thereof specified in the access request 302, etc. In some examples, the data rights definition may be stored as a part of the data structure that includes the shared data, as described with reference to FIG. 13.

The method 1400 further includes comparing the first key to the second key, at 1408, and, based on the comparison, determining whether to grant the second computing device access to the first data but not the second data. When the first key "matches" the second key (e.g., the keys are identical or can be mathematically verified, as in public/private key pairs), the method 1400 includes granting the second computing device access to the first data but not the second data, at 1410. For example, in FIG. 3, the first measurement system 310 may send the copy 304 of the shared data 340 to the second measurement system. Conversely, when the first key does not "match" the second key, the method 1400 includes denying the access request, at 1412.

In some examples, granting the second computing device access to the first data includes sending a copy of the first data to the second computing device for storage in a second data structure at the second computing device. Thus, in particular embodiments a portion of one or more of the data structures described herein (e.g., the bitmap indexes 126, 132, 134 of FIG. 1, the bitmap index 550 of FIG. 5, etc.) may store a copy of data that has been received from a grantor based on a data rights definition. In such examples, the copy of the data may be synchronized with the "master" copy at the grantor. For example, the method 1400 may include receiving a write operation with respect to the first data, performing the write operation on the first data, and causing the write operation to be replicated at the copy of the first data in the second data structure, at 1414. To illustrate, referring to FIG. 3, the first measurement system 310 may receive the event signal 306, modify bit(s) of the bitmap index stored in the first data storage 312 in response to the event signal 306, and send the message 308 causing the write operation to be replicated at the bitmap index stored in the second data storage 322. Synchronization of shared data may be performed responsive to a push synchronization operation initiated by the first measurement system 310 or responsive to a pull synchronization operation initiated by the second measurement system 320 (e.g., in response to the synchronization request 309).

Figure 15:
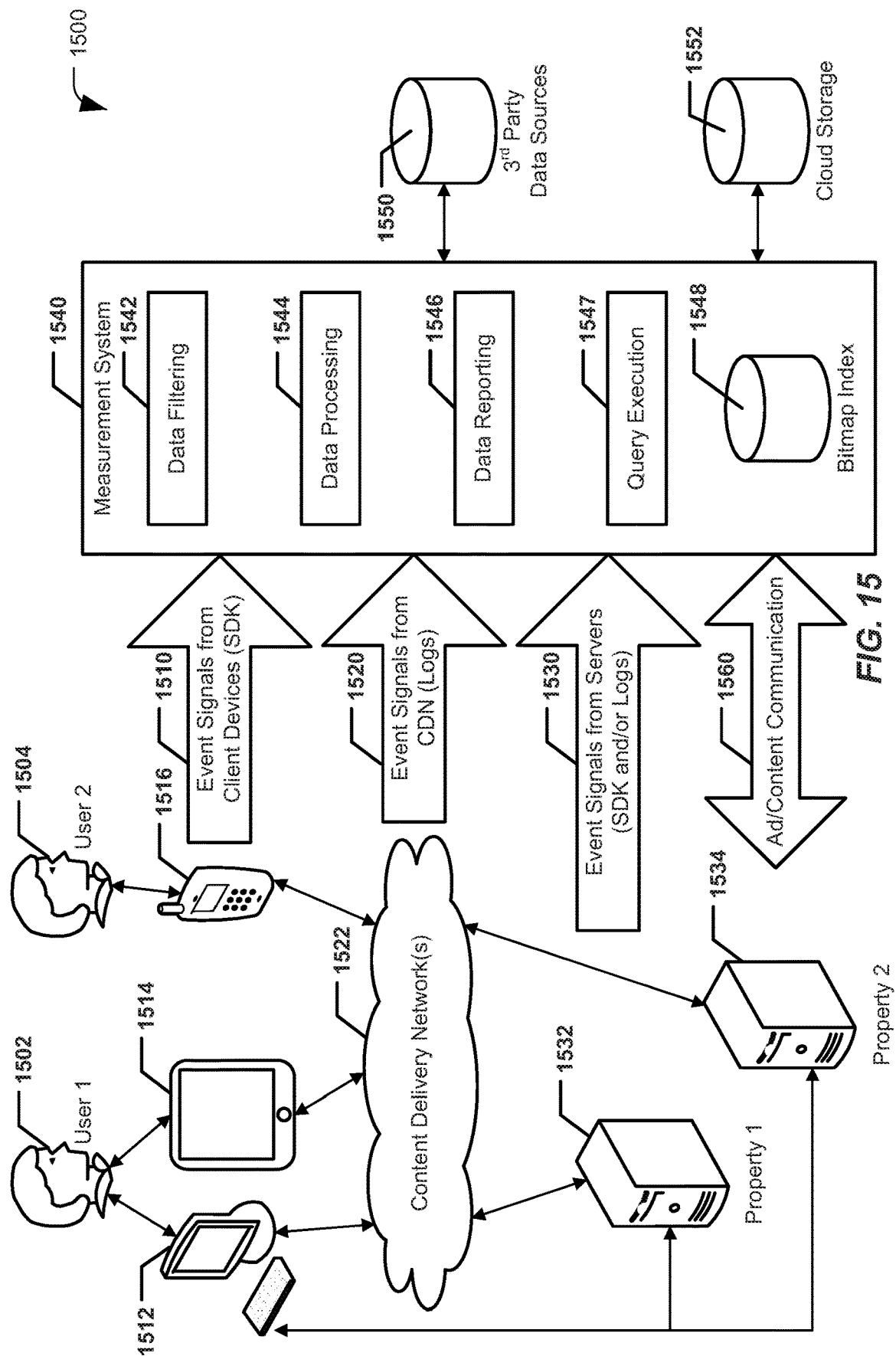
FIG. 15 is a diagram to illustrate a particular embodiment of an audience measurement system that is operable to generate and use a bitmap index.

The bitmap index described herein may thus enable a measurement system, such as the measurement system 120, to quickly provide analysis for "raw" data stored in an offsite (e.g., cloud-based) storage location. The bitmap index may represent an on-the-fly index of binary representations of different audience traits that can be mined to determine what set of audience members is most likely to be receptive to particular content, a particular advertisement, etc. Audience traits may be combined into long bit strings, where each bit string represents a single trait for an entire audience. By keeping the bitmap index "hot" in memory, ad-hoc queries may be performed efficiently and with reduced latency, and the results of such queries can include metadata regarding the audience traits and/or audience members. Moreover, all or a portion of the bitmap index may be shared with other entities in accordance with previously established data rights definitions. The described techniques may also be used with other types of systems. For example, in alternate embodiments, the same location in each bit string of the bitmap index may correspond to an identifier other than a user ID, such as an inventory number, an employee number, a hospital patient identifier, etc. In some examples, the bitmap index includes a plurality of bit strings, where a value stored in a particular location in each of the bit strings indicates whether a corresponding signal associated with a signal source has been received. As illustrative non-limiting examples, a signal source may include a user, a computing device associated with the user, or a computing device not associated with any user (e.g., an IoT device). FIGS. 15 and 16 illustrate additional scenarios in which a bitmap index may be generated and used.

In particular, FIG. 15 illustrates an alternate embodiment of a measurement system and is generally designated 1500. A measurement system 1540 may be communicatively coupled to one or more user devices (e.g., illustrative user devices 1512, 1514, and 1516), to one or more content delivery networks (CDNs) (e.g., illustrative CDN 1522), and to properties (e.g., websites) 1532 and 1534. In FIG. 15, the properties 1532 and 1534 are illustrated by corresponding servers (e.g., web servers). The measurement system 1540 may be implemented using one or more computing devices (e.g., servers). For example, such computing devices may include one or more processors or processing logic, memories, and network interfaces. The memories may include instructions executable by the processors to perform various functions described herein. The network interfaces may include wired and/or wireless interfaces operable to enable communication to local area networks and/or wide area networks (e.g., the Internet).

The user devices 1512-1516 may be associated with various users. For example, the desktop computing device 1512 and the tablet computing device 1514 may be associated with a first user 1502, and the mobile telephone device (e.g., smartphone) 1516 may be associated with a second user 1504. It should be noted that the user devices 1512-1516 are shown for example only and are not to be considered limiting. In alternate embodiments, fewer, additional, and/or different types of user devices may be present in the system 1500. For example, a radio-frequency identification (RFID)-enabled device may be carried by a user and may transmit a signal in response to detecting that the user is visiting a particular physical location. In a particular embodiment, the user devices 1512-1516 may execute applications that are operable to access the properties 1532 and 1534. For example, the user devices 1512-1516 may include applications developed using a mobile software development kit (SDK) that includes support for audience measurement functions. To illustrate, when the SDK-based applications interact with the properties 1532 and 1534, the applications may generate first event signals 1510 that are transmitted by the user devices 1512-1516 to the measurement system 1540.

The first event signals 1510 may include information identifying specific interactions by the users 1502-1504 via the user devices 1512-1516 (e.g., what action was taken at a media property, when the action was taken, for how long the action was taken, etc.). The user interactions may include interactions with advertisements presented by the media property and/or interactions with content presented by the media property. The event signals 1510 may also include an identifier, such as a browser identifier (browser ID) generated by the SDK. In a particular embodiment, browser identifiers are unique across software installations and devices. For example, a first installation of a SDK-based application at the desktop computing device 1512 and a second installation of the same SDK-based application at the tablet computing device 1514 may use different browser IDs, even though both installations are associated with the same user 1502.

In another particular embodiment, Browser IDs may remain consistent until applications or web browsers are "reset" (e.g., caches/cookies are cleared). In some embodiments, the user devices 1512-1516 may execute applications other than browser applications, such as downloadable mobile applications, that generate the event signals 1510 based on user interactions with advertisements and/or content presented by the applications.

The user devices 1512-1516 may access content provided by the properties 1532 and 1534 directly or via the CDN 1522. The CDN 1522 may provide distributed, load-balanced access to audio, video, graphics, and web pages associated with the media properties 1532 and 1534. For example, the CDN 1522 may include geographically distributed web servers and media servers that serve Internet content in a load-balanced fashion. The CDN 1522 may send second event signals 1520 to the measurement system 1540. The second event signals 1520 may include information identifying interactions with media properties and browser IDs provided to the CDN 1522 by the user devices 1512-1516 and/or the properties 1532 and 1534. For example, the second event signals 1520 may include CDN logs or data from CDN logs.

The media properties 1532 and 1534 may be controlled by the same entity (e.g., may be part of a federated property) or by different entities. The properties 1532 and 1534 may send third event signals 1530 to the measurement system 1540. The third event signals 1530 may include information identifying interactions with the media properties and browser IDs provided by the user devices 1512-1516 during communication with the properties 1532 and 1534 (e.g., communication via hypertext transfer protocol (HTTP), transport control protocol/internet protocol (TCP/IP), or other network protocols).

In a particular embodiment, the third event signals 1530 may include server logs or data from server logs. Alternately, or in addition, the third event signals 1530 may be generated by SDK-based (e.g., web SDK-based) applications executing at the properties 1532 and 1534, such as scripts embedded into web pages hosted by the properties 1532 and 1534.

The first event signals 1510 from the user devices 1512-1516 and the second event signals 1520 generated by the CDN 1522 may be considered "first-party" event signals. The third event signals 1530 from the properties 1532 and 1534 may be considered "third-party" event signals. First party event signals may be considered more trustworthy and reliable than third party event signals, because of the possibility that third party event signals could be modified by a media property owner prior to transmission to the measurement system 1540.

In a particular embodiment, the properties 1532 and 1534 may send data to the measurement system 1540 and receive data from the measurement system 1540 regarding advertisements and/or content presented by the properties 1532 and 1534. Such communication is illustrated in FIG. 15 as advertisement/content communication 1560. For example, an advertisement (or software associated with the advertisement that is executing on a client device, such as web server, a computer, a mobile phone, a tablet device, etc.) may collect and transmit data on a per-advertisement, per-user basis. The data may include or identify a profile of a user, a duration that the user viewed the advertisement, action(s) performed by the user with respect to the advertisement, etc. As another example, a content item or software associated therewith may collect and transmit data regarding user interactions with the content item.

In a particular embodiment, the measurement system 1540 includes a data filtering module 1542, a data processing module 1544, a data reporting module 1546, and a query execution module 1547. In a particular embodiment, each of the modules 1542-1547 is implemented using instructions executable by one or more processors at the measurement system 1540.

The data filtering module 1542 may receive the event signals 1510, 1520, and 1530. The data filtering module 1542 may check the event signals 1510, 1520, and 1530 for errors and may perform data cleanup operations when errors are found. The data filtering module 1542 may also receive and perform cleanup operations on advertisement measurement data and content measurement data received from the properties 1532 and 1534 and from applications executing on the user devices 1512-1516. In a particular embodiment, the data filtering module 1542 may implement various application programming interfaces (APIs) for event signal collection and inspection. The data filtering module 1542 may store authenticated/verified event signals in a database, event cache, archive, and/or cloud storage 1552. In a particular embodiment, the measurement system 1540 includes or has access to a brand database that tracks brands. For example, "raw" data corresponding to the brand database and other collected data may be stored in the cloud storage 1552. Signals received from the properties 1532 and 1534 and from applications executing the user devices 1512-1516 may identify a brand that matches one of the brands in the brand database. The measurement system 1540 may thus track advertisements/content for various brands across multiple properties.

The data processing module 1544 may operate as described with reference to the data processing module 152 of FIG. 1. Alternately, or in addition, the data processing module 1544 may associate received event signals (and interactions represented thereby) with user profiles of users. For example, when an event signal having a particular browser ID is a social networking registration event (e.g., when a user logs into a website using a Facebook® account, a Twitter® account, a LinkedIn® account, or some other social networking account), the data processing module 1544 may retrieve a corresponding social networking profile or other user profile data from third party data sources 1550. Facebook is a registered trademark of Facebook, Inc. of Menlo Park, Calif. Twitter is a registered trademark of Twitter, Inc. of San Francisco, Calif. LinkedIn is a registered trademark of LinkedIn Corp. of Mountain View, Calif.

It will be appreciated that interactions that were previously associated only with the particular browser ID (i.e., "impersonal" alphanumeric data) may be associated with an actual person (e.g., John Smith) after retrieval of the social networking profile or user profile. Associating interactions with individuals may enable qualitative analysis of the audiences of media properties. For example, if John Smith is a fan of a particular sports team, the measurement system 1540 may indicate that at least one member of the audience of the first property 1532 or the second property 1534 is a fan of the particular sports team. When a large percentage of a media property's audience shares a particular characteristic or interest, the media property may use such information in selecting and/or generating advertising or content. User profiles (e.g., a profile of the user John Smith) and audience profiles (e.g., profiles for the media properties associated with the properties 1532 and 1534) may be stored in the cloud storage 1552 and/or in another database. An audience profile for a particular media property may be generated by aggregating the user profiles of the individual users (e.g., including John Smith) that interacted with the particular media property.

Audience profiles may be generated using as few as one or two user profiles, although any number of user profiles may be aggregated. In a particular embodiment, audience profiles may be updated periodically (e.g., nightly, weekly, monthly, etc.), in response to receiving updated data for one or more users in the audience, in response to receiving a request for audience profile data, or any combination thereof. Audience profiles may similarly be generated for audiences of a particular mobile application based on signals generated by installations of the mobile application on various user devices.

The data reporting module 1546 may generate various interfaces. The data reporting module 1546 may also support an application programming interface (API) that enables external devices to view and analyze data collected and stored by the measurement system 1540. In a particular embodiment, the data reporting module 1546 is configured to segment the data.

As used herein, a "segment" is based on a group of people (e.g., an audience or a subset thereof). As further described herein, a digital genome may be determined for each segment. Examples of segments include, but are not limited to, brand affinity segments (also called brand segments), demographic segments, geographic segments, social activity segments, employer segments, educational institution segments, professional group segments, industry category of employer segments, brand affinity category segments, professional skills segments, job title segments, and behavioral segments. In a particular embodiment, behavioral segments are defined by a client (e.g., property owner or publisher) or by the measurement system 1540, and represent actions taken on a client's property.

Additional examples of segments include segments based on an advertisement, an advertisement campaign, an advertisement placement, an advertisement context, a content item, a content context, content placement, a platform (e.g., desktop/laptop computer vs. mobile phone vs. tablet computer), etc. Segments may be used to understand or evaluate characteristics of an audience, craft a content strategy, generate advertising leads, create advertising pitches, and respond to inbound advertising requests. Segments may also be used to acquire additional audience members, receive information from advertisements/content items, and send information to advertisements/content items. In a particular embodiment, the measurement system 1540 may be operable to define "new" segments based on performing logical operations (e.g., logical OR operations and logical AND operations).

The measurement system 1540 may also include a bitmap index 1548 (e.g., the bitmap index 126 of FIG. 1 and/or the bitmap index 550 of FIG. 5). The bitmap index 1548 may store bit strings corresponding to at least a subset of the "raw" data stored in the cloud storage 1552. In one example, a different bitmap index 1548 is maintained for each property 1532, 1534. The bitmap index 1548 for a particular property may include, for each audience member of the property, data regarding a demographic attribute of the audience member, a brand affinity of the audience member, and/or behaviors (e.g., interactions with the media property) of the audience member. The same location in each bit string of the bitmap index 1548 may correspond to the same user.

The data processing module 1544 may also be configured to, upon receiving an event signal, parse the event signal to identify what user and media property the event signal corresponds to. The data processing module 1544 may store data corresponding to the event signal in one or more databases (e.g., the cloud storage 1552, a user profile database, etc.). The data processing module 1544 may also store indexing data corresponding to the event signal in the bitmap index 1548 for the identified media property. If the user is a new audience member for the media property, the data processing module 1544 may assign a new ID to the user. Event signals may be processed as described above with reference to FIGS. 1-12.

The query execution module 1547 may operate as described with reference to the query execution module 124 of FIG. 1 and/or the query execution module 1106 of FIG. 11. For example, the query execution module 1547 may receive a query and generate a query execution plan that parallelizes execution and reduces/minimizes data transfers between storage nodes during query execution.

During operation, the users 1502-1504 may interact with the media properties 1532 and 1534 and with applications executing on the user devices 1512-1516. In response to the interactions, the measurement system 1540 may receive the event signals 1510, 1520, 1530, and/or 1560. Each event signal may include a unique identifier, such as a browser ID and/or an audience member ID. If the user is a "new" audience member, the data processing module 1544 may create a user profile. Data for the user profile may be stored in the cloud storage 1552 and/or the bitmap index 1548. In a particular embodiment, data for the user profile may be retrieved from the third party data sources 1550.

For example, the data processing module 1544 may retrieve and store data from one or more social network profiles of the user. The data may include demographic information associated with the user (e.g., a name, an age, a geographic location, a marital/family status, a homeowner status, etc.), social information associated with the user (e.g., social networking activity of the user, social networking friends/likes/interests of the user, etc.), and other types of data. The data processing module 1544 may also collect and store data associated with advertisements and content served by the properties 1532 and 1534 and by applications executing on the user devices 1512-1516. In a particular embodiment, the measurement system 1540 is further configured to receive offline data from external data sources. For example, the measurement system 1540 may receive data regarding transactions (e.g., purchases) made by an audience and may use the transaction data to generate additional signals that contribute to the digital genome of an audience, brand, property, etc. Another example of offline data may be a "data dump" of data collected by an RFID-enabled device or an RFID detector. Offline data may be stored in one or more computer-readable files that are provided to the measurement system 1540. In a particular embodiment, offline data can include previously collected data regarding users or audience members (e.g., names, addresses, etc.).

The data reporting module 1546 may report data collected by the measurement system 1540. For example, the data reporting module 1546 may generate reports based on an audience profile of a media property (or application), where the audience profile is based on aggregating user profiles of users that interacted with the media property (or application). To illustrate, the data reporting module 1546 may generate an interface indicating demographic attributes of the audience as a whole (e.g., a percentage of audience members that are male or female, percentages of audience members in various age brackets, percentages of audience members in various income bracket, most common audience member cities/states of residence, etc.). The interface may also indicate social attributes of the audience as a whole (e.g., the most popular movies, sports teams, etc. amongst members of the audience). Audience profiles may also be segmented and/or aggregated with other audience profiles, as further described herein. Audience profiles may further be segmented based on advertisement, advertisement campaign, brand, content item, etc. Audience profiles may also be constructed by combining segments, as further described herein.

In a particular embodiment, the system 1500 may also receive event signals based on measurements (e.g., hardware measurements) made at a device. For example, an event signal from the tablet computing device 1514 or the mobile telephone device 1516 may include data associated with a hardware measurement at the tablet computing device 1514 or the mobile telephone device 1516, such as an accelerometer or gyroscope measurement indicating an orientation, a tilt, a movement direction, and/or a movement velocity of the tablet computing device 1514 or the mobile telephone device 1516. As another example, the system 1500 may receive a signal in response to an RFID device detecting that a user is visiting a particular physical location. The system 1500 of FIG. 15 may also link interactions with user profiles of users. This may provide information of "how many" viewers and "how long" the viewers watched a particular video (e.g., as in direct response measurement systems), and also "who" watched the particular video (e.g., demographic, social, and behavioral attributes of the viewers).

The system 1500 of FIG. 15 may thus enable audience measurement and analysis based on data (e.g., event signals) received from various sources. Further, the system 1500 of FIG. 15 may enable real-time or near-real time execution of queries on collected data, such as execution of "top N" queries using the bitmap index 1548.

Figure 16A:
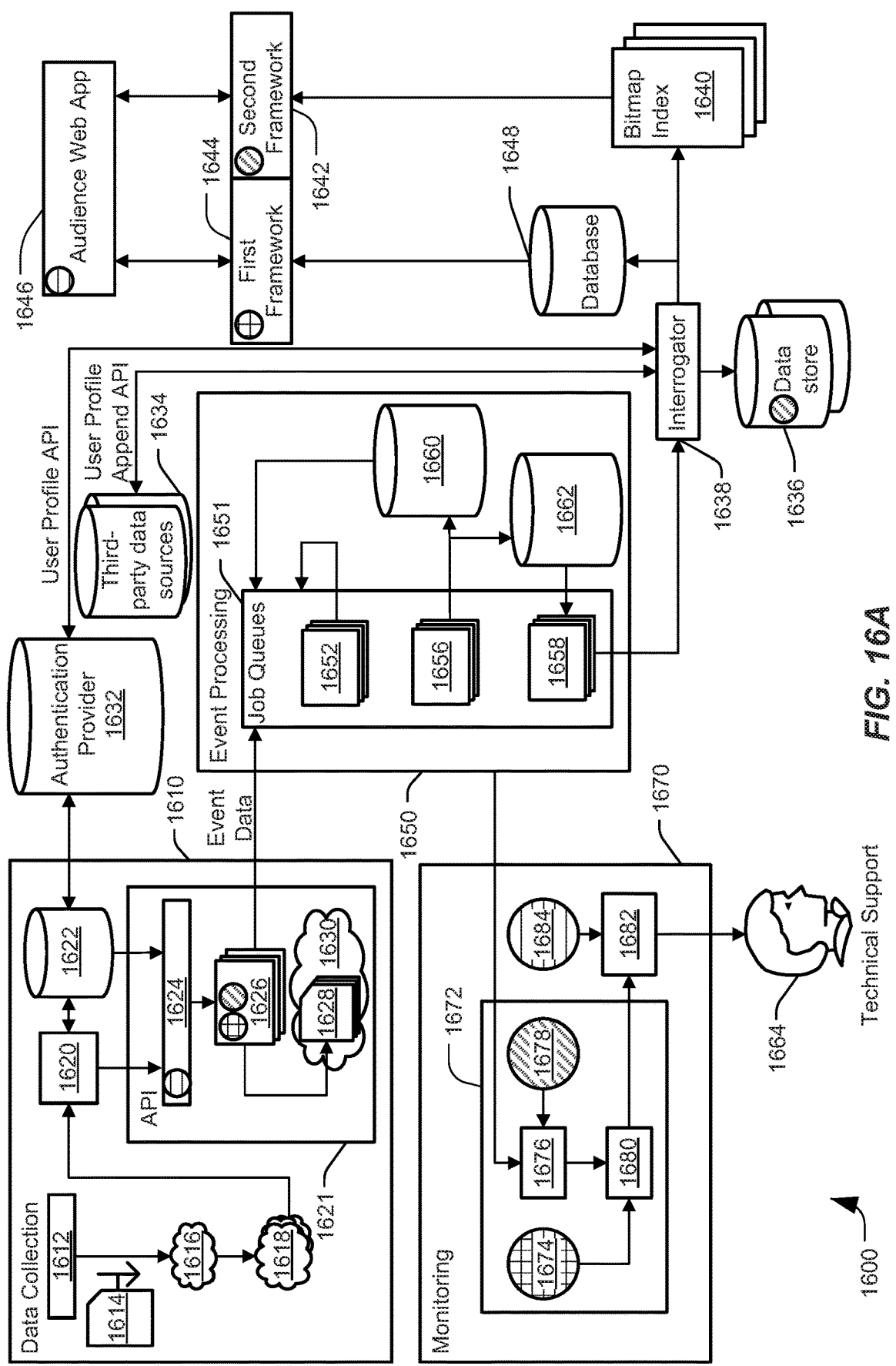
FIGS. 16A, 16B, 16C, and 16D are diagrams to illustrate another particular embodiment of an audience measurement system that is operable to generate and use a bitmap index.
Figure 16B:
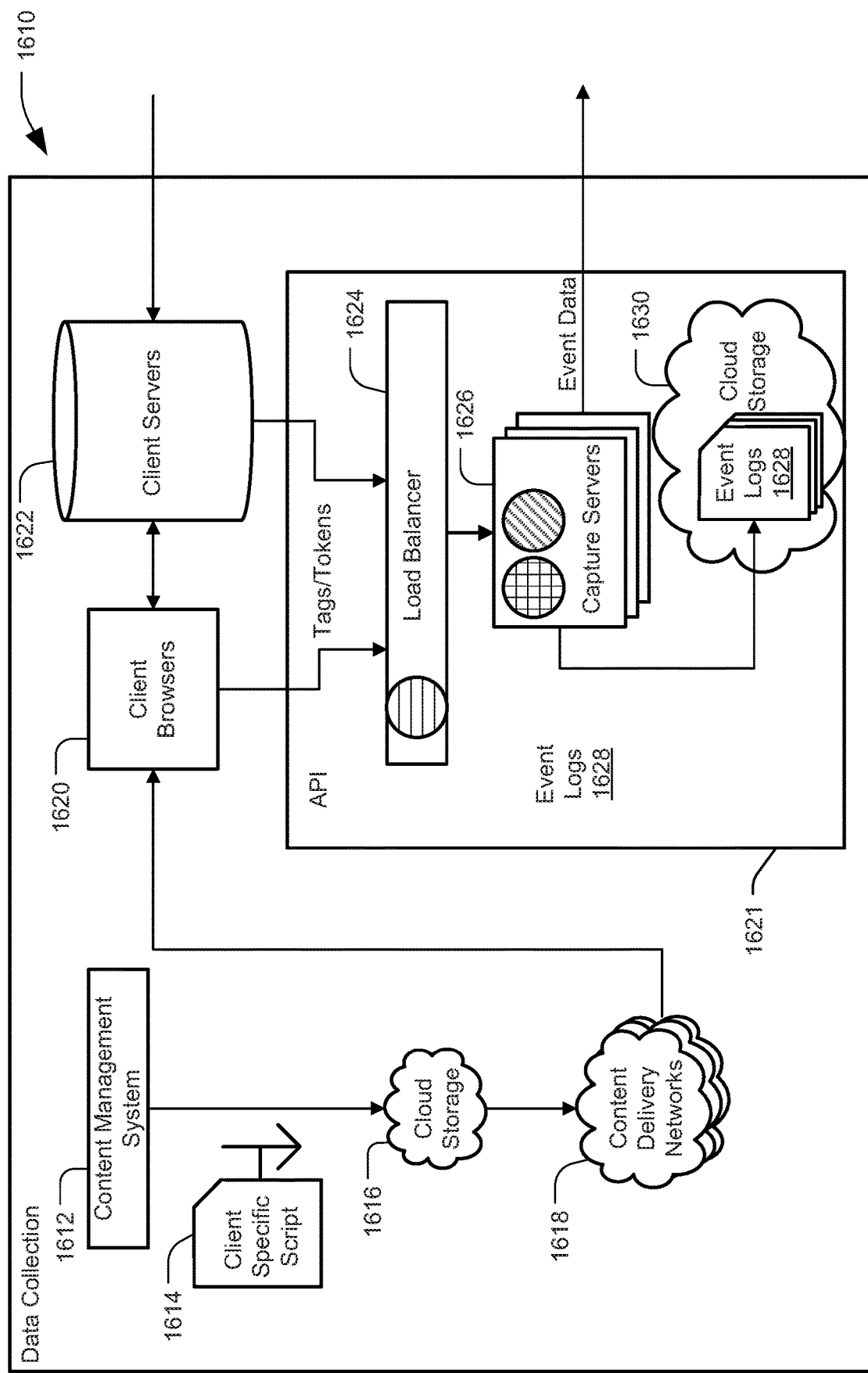
Figure 16C:
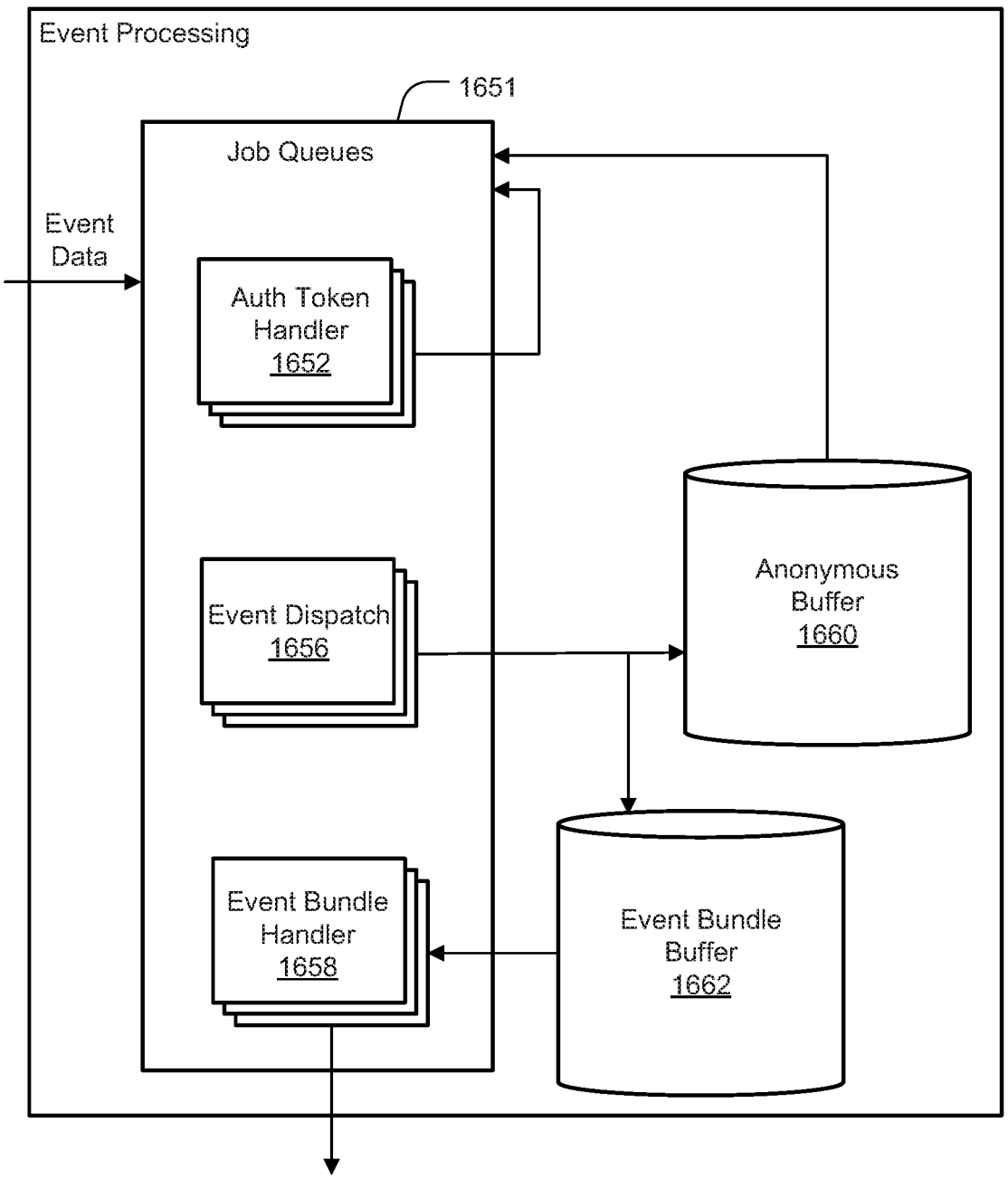
Figure 16D:
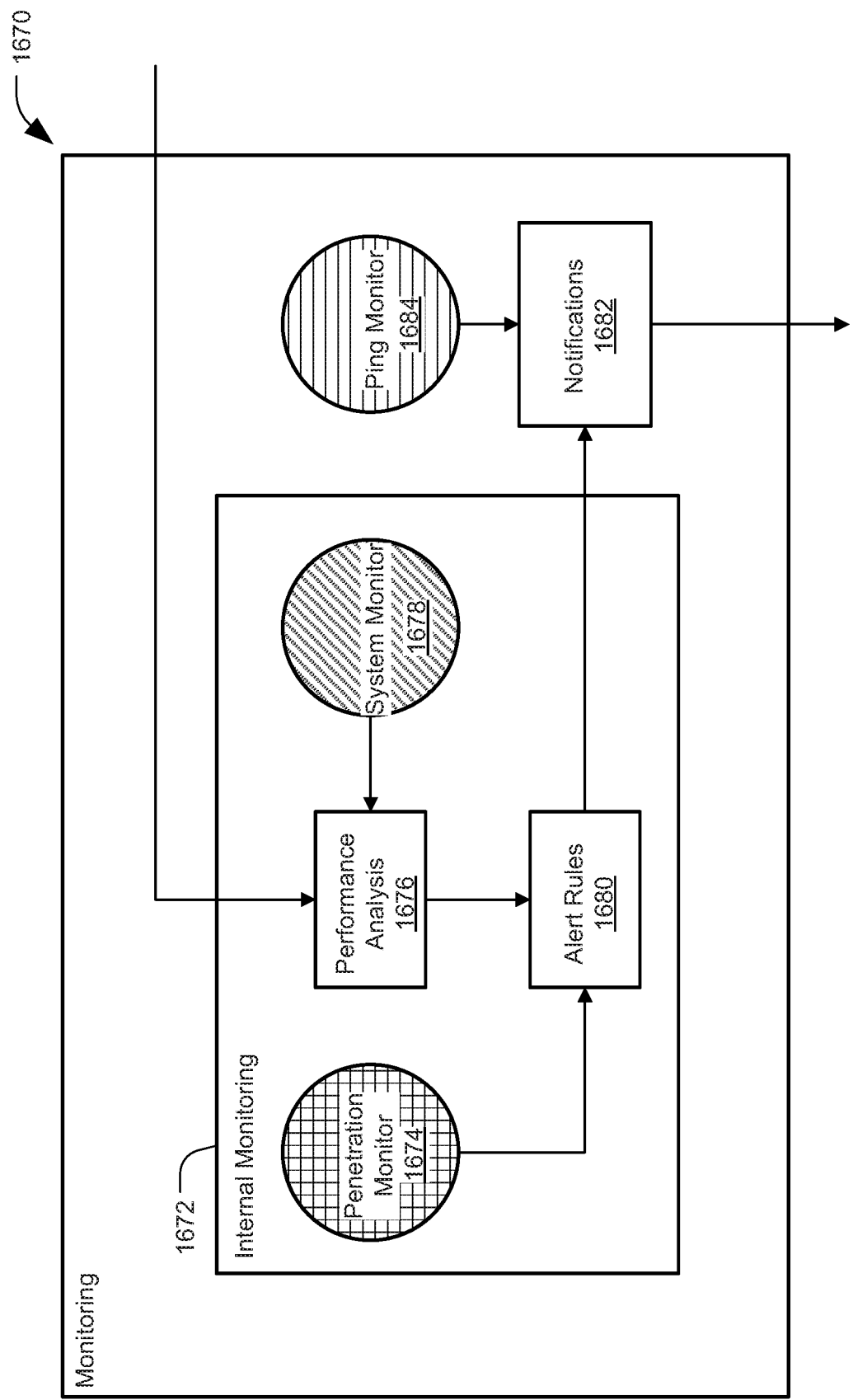

FIG. 16A illustrates another particular embodiment of a system 1600 that is operable to generate and use a bitmap index. The system 1600 includes a data collection tier (e.g., subsystem) 1610, an event processing tier 1650, and a monitoring tier 1670. Components of the data collection tier 1610 are illustrated in further detail in FIG. 16B. Components of the event processing tier 1650 are illustrated in further detail in FIG. 16C. Components of the monitoring tier are illustrated in further detail in FIG. 16D.

The system 1600 includes (or has access to) an authentication provider 1632, third party data sources 1634, an audience web application 1646, a first framework 1644, a second framework 1642, a database 1648, an interrogator 1638, a data store 1636, and a bitmap index 1640. In an illustrative embodiment, the third party data sources 1634 are the third party data sources 1550 of FIG. 15, the event processing tier 1650 and the interrogator 1638 correspond to the data processing module 1544 of FIG. 15, and the bitmap index 1640 is the bitmap index 1548 of FIG. 15.

The data collection tier 1610 includes a content management system (CMS) 1612, cloud storage 1616, content delivery networks 1618, client browsers 1620, and client servers 1622. The data collection tier 1610 may further include an application programming interface (API) 1621. The API 1621 includes a load balancer 1624, capture servers 1626, and cloud storage 1630.

The event processing tier 1650 includes a job queues module 1651, an anonymous buffer 1660, and an event bundle buffer 1662. The job queues module 1651 includes an authentication token handler 1652, an event dispatch 1656, and an event bundle handler 1658. In alternate embodiments, the job queues module 1651 may include more, fewer, and/or different handlers than illustrated in FIG. 16.

The monitoring tier 1670 includes an internal monitoring module 1672, a ping monitor 1684, and a notifications module 1682. The internal monitoring module 1672 includes a penetration monitor 1674, a performance analysis module 1676, a system monitor 1678, and an alert rules module 1680.

During operation, the content management system 1612 may be used to generate a client specific script (e.g., webscript) 1614 for various clients (e.g., media properties). The client specific script 1614 may be stored in the cloud storage 1616 and replicated to the content delivery networks 1618. As audience members register and interact with a media property, the content delivery networks 1618 may deliver the client specific script 1614, along with property content, to the client browsers 1620. Based on the client specific script 1614, the client browsers 1620 may generate tags (e.g., a tag corresponding to a particular user activity, such as watching a video) or tokens (e.g., a social networking registration token). The tags or tokens may be sent to the load balancer 1624. The client servers 1622 may also generate tags or tokens to send to the load balancer 1624 based on user registrations and user activity at media properties. The tags or tokens from the client servers 1622 may be authenticated by the authentication provider 1632.

The load balancer 1624 may send the tags or tokens to the capture servers 1626 based on a load balancing algorithm. The capture servers 1626 may generate event data (e.g., event signals) based on the tags or tokens. The capture servers 1626 may store the event data in event logs 1628 in the cloud storage 1630 and send the event data to the job queues module 1651.

The job queues module 1651 may distribute the event data to different event handler(s) based on the type of the event data. For example, event data including an authentication token may be sent to the authentication token handler 1652. In addition, event data requiring additional information from social media sources may be sent to the authentication token handler 1652. The handler 1652 may perform asynchronous event collection operations based on the received event data. For example, when a new user registers with a media property using a social networking profile, a token may be provided by the data collection tier to the authentication token handler 1652. The handler 1652 may use the token to retrieve demographic and brand affinity data for the user from the user's social networking profile.

Event signals may also be sent to the event dispatch 1656, which determines whether the event signals corresponds to known or unknown users. When event data corresponds to an unknown user, the event dispatch 1656 buffers the event data in the anonymous buffer 1660. After a period of time (e.g., three days), event data from the anonymous buffer 1660 may be sent to the job queues module 1651 to be processed again.

When event data corresponds to a "known" user (e.g., a user that has already been assigned a user ID), the event dispatch 1656 may send the event data to the event bundles buffer 1662. The event bundle handler 1658 may retrieve event data stored in the event bundles buffer 1662 every bundling period (e.g., one hour). The event bundle handler 1658 may bundle event data received each bundling period into an event bundle that is sent to the interrogator 1638.

The interrogator 1638 may parse the event bundle and update the data store 1636, the SQL database 1648, and/or the bitmap index 1640. For example, the interrogator 1638 may perform bitmap index generation and update operations as described herein. In a particular embodiment, the database 1648 corresponds to a profiles database that is accessible the first framework 1644 to the audience web application 1646. For example, the first framework 1644 may be a database-driven framework that is operable to dynamically generate webpages based on data in the database 1648. The audience web application may be operable to generate various graphical user interfaces to analyze the data collected by the system 1600. The bitmap index 1640 may be accessible to the audience web application 1646 via the second framework 1642. In one example, the second framework 1642 supports representational state transfer (REST)-based data access and webpage navigation. Although not shown, in particular embodiments, the data store 1636 may also be accessible to the audience web application 1646.

The monitoring tier 1670 may monitor the various components of the system 1600 during operation to detect errors, bottlenecks, network intrusions, and other issues. For example, the penetration monitor 1674 my collect data indicating unauthorized access to or from the capture servers 1626 and the first framework 1644. The penetration monitor 1674 may provide the data to the alert rules module 1680. Similarly, the system monitor 1678 may collect performance data from the capture servers 1626, from the second framework 1642, and from the data store 1636. The system monitor 1678 may provide the performance data to the performance analysis module 1676, which may analyze the data and send the analyzed data to the alert rules module 1680. The alert rules module 1680 may compare received data to alert rules and, based on the comparison send an alert to the notifications module 1682. For example, the alert rules module 1680 may determine that an intruder has accessed components of the system 1600 or that the system 1600 is not operating at a desired level of efficiency, and may send an alert to the notifications module 1682.

The notifications module 1682 may also receive alerts from the ping monitor 1684. The ping monitor 1684 may monitor the load balancer 1624 and the audience web application 1646 and collect data regarding uptime, downtime, and performance, and provide alerts to the notification module 1682.

The notification module 1682 may send notifications (e.g., via short message service (SMS), e-mail, instant messaging, paging, etc.) to one or more technical support staff members 1664 to enable timely response in the event of errors, performance bottlenecks, network intrusion, etc.

In accordance with various embodiments of the present disclosure, the methods, functions, and modules described herein may be implemented by software programs executable by a computer system. Further, in an exemplary embodiment, implementations can include distributed processing, component/object distributed processing, and parallel processing. Alternatively, virtual computer system processing can be constructed to implement one or more of the methods or functionality as described herein.

Particular embodiments can be implemented using a computer system executing a set of instructions that cause the computer system to perform any one or more of the methods or computer-based functions disclosed herein. A computer system may include a laptop computer, a desktop computer, a mobile phone, a tablet computer, a set-top box, a media player, or any combination thereof. The computer system may be connected, e.g., using a network, to other computer systems or peripheral devices. For example, the computer system or components thereof can include or be included within any one or more devices, modules, and/or components illustrated in FIGS. 1-16. In a networked deployment, the computer system may operate in the capacity of a server or as a client user computer in a server-client user network environment, or as a peer computer system in a peer-to-peer (or distributed) network environment. The term "system" can include any collection of systems or sub-systems that individually or jointly execute a set, or multiple sets, of instructions to perform one or more computer functions.

In a particular embodiment, the instructions can be embodied in a computer-readable or a processor-readable device. The terms "computer-readable device" and "processor-readable device" include a single storage device or multiple storage devices, such as a centralized or distributed database, and/or associated caches and servers that store one or more sets of instructions. The terms "computer-readable device" and "processor-readable device" also include any device that is capable of storing a set of instructions for execution by a processor or that cause a computer system to perform any one or more of the methods or operations disclosed herein. For example, a computer-readable or processor-readable device or storage device may include random access memory (RAM), flash memory, read-only memory (ROM), programmable read-only memory (PROM), erasable programmable read-only memory (EPROM), electrically erasable programmable read-only memory (EEPROM), registers, a hard disk, a removable disk, a disc-based memory (e.g., compact disc read-only memory (CD-ROM)), or any other form of storage device. A computer-readable or processor-readable device is not a signal.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Accordingly, the disclosure and the figures are to be regarded as illustrative rather than restrictive.

Although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments.

The above-disclosed subject matter is to be considered illustrative, and not restrictive, and the appended claims are intended to cover all such modifications, enhancements, and other embodiments, which fall within the true scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A method comprising:
    receiving, at a first computing device from a second computing device, an access request specifying first data stored in a first portion of a data structure and second data stored in a second portion of the data structure, wherein the data structure comprises a bitmap index that includes multiple data rights definitions corresponding to the first data and multiple data rights definitions corresponding to the second data, wherein at least one of the data rights definitions comprises row information, column information, and bit information, wherein the bitmap index includes a plurality of bit strings, and wherein a value stored in a particular location in each of the bit strings indicates whether a corresponding signal associated with a signal source has been received;

extracting a first key from the access request;

identifying a particular data rights definition that is associated with the data structure and that is associated with a second key, the particular data rights definition indicating that the first data but not the second data is shared with an entity associated with the second computing device; and based on comparing the first key to the second key, determining whether to grant the second computing device access to the first data but not the second data.

2. The method of claim 1, wherein a first bit string in the bitmap index corresponds to the first data, wherein a second bit string in the bitmap index corresponds to a first data right associated with the first data, wherein a third bit string in the bitmap index corresponds to a second data right associated with the first data, and wherein a fourth bit string in the bitmap index corresponds to the second data.

3. The method of claim 1, wherein the data structure comprises a database table.

4. The method of claim 1, wherein the signal source corresponds to a user, an electronic device associated with the user, or an internet of things (IoT) device.

5. The method of claim 1, wherein the first data is associated with at least one patient, medical staff, medical equipment, at least one medical location, at least one medicine, at least one healthcare event, at least one medical attribute, or any combination thereof, and wherein the second data is associated with at least one demographic attribute, at least one behavior, at least one brand affinity, or any combination thereof.

6. The method of claim 1, wherein the first data is associated with at least one investor, at least one financial advisor, at least one financial product, at least one account, at least one investment, or any combination thereof, and wherein the second data is associated with at least one customer, at least one product in inventory, or any combination thereof.

7. The method of claim 1, wherein the bitmap index stores data associated with at least one internet of things (IoT) device, at least one sensor reading, at least one communication by the IoT device, at least one status of the IoT device, at least one event observed by the IoT device, or any combination thereof.

8. The method of claim 1, wherein the particular data rights definition is stored in a repository that stores a plurality of data rights definitions associated with a plurality of data structures and a plurality of entities.

9. The method of claim 1, wherein the multiple data rights definitions are included in a third portion of the data structure that is distinct from the first portion and the second portion.

10. The method of claim 1, wherein the particular data rights definition further indicates:

whether the entity associated with the second computing device has read-only access to the first data or read-write access to the first data, that the first data is shared with the entity associated with the second computing device for a particular time period, whether personally identifiable information associated with the first data is shared with the entity associated with the second computing device, or any combination thereof.

11. A non-transitory computer readable medium having program instructions stored therein that are executable to perform operations comprising:

receiving an access request at a first computing device from a second computing device, the access request specifying first data stored in a first portion of a data structure and further specifying second data stored in a second portion of the data structure, wherein the data structure comprises a bitmap index that includes multiple data rights definitions corresponding to the first data and multiple data rights definitions corresponding to the second data, wherein the bitmap index includes a plurality of bit strings, and wherein a value stored in a particular location in each of the bit strings indicates whether a corresponding signal associated with a signal source has been received;

identifying a particular data rights definition associated with the access request, the particular data rights definition indicating that the first data but not the second data is shared with an entity associated with the second computing device; and granting access to the first data but not the second data based on the particular data rights definition.

12. The computer readable medium of claim 11, wherein the data structure is arranged as a table including a plurality of data columns and a plurality of data rows, wherein the first data includes a first set of data columns of the plurality of data columns, and wherein the second data comprises a second set of data columns of the plurality of data columns, the first set of data columns distinct from the second set of data columns.

13. The computer readable medium of claim 11, wherein the particular data rights definition is stored in a repository that stores a plurality of data rights definitions associated with a plurality of data structures and a plurality of entities.

14. The computer readable medium of claim 11, wherein granting access to the first data comprises sending a copy of the first data to the second computing device for storage in a second data structure at the second computing device.

15. The computer readable medium of claim 14, the operations further comprising:

receiving a write operation with respect to the first data; and initiating performance of the write operation at the copy of the first data in the second data structure.

16. The computer readable medium of claim 15, wherein the write operation is replicated responsive to a push synchronization operation initiated by the first computing device or responsive to a pull synchronization operation initiated by the second computing device or by another computing device associated with an entity.

17. A system, comprising:

a processor; and a memory accessible to the processor, wherein the memory includes:

a data structure comprising at least first data stored in a first portion of the data structure and second data stored in a second portion of the data structure, wherein the data structure comprises a bitmap index that includes multiple data rights definitions, wherein the first data corresponds to a first plurality of data rights definitions of the multiple data rights definitions and the second data corresponds to a second plurality of data rights definitions of the multiple data rights definitions, wherein the bitmap index includes a plurality of bit strings, and wherein a value stored in a particular location in each of the bit strings indicates whether a corresponding signal associated with a signal source has been received; and instructions that, when executed by the processor, cause the processor to:

receive a data request received from a client computer to access the first data and the second data;

identify a particular data rights definition associated with the data request, the particular data rights definition indicating that the first data but not the second data is shared with an entity associated with the client computer; and based on the particular data rights definition, initiate sending the first data but not the second data to the client computer.

18. The system of claim 17, wherein the instructions, when executed by the processor, further cause the processor to, in response to a second data request received from a second client computer to access the data structure, initiate sending the second data but not the first data to the second client computer, and wherein the second data request indicates second data rights that correspond to the second plurality of data rights definitions but not the first plurality of data rights definitions.

19. The system of claim 17, wherein the data structure comprises a database table.

* * * * *